US012646607B2

(12) United States Patent
Neumann et al.

(10) Patent No.: US 12,646,607 B2
(45) Date of Patent: Jun. 2, 2026

(54) SELF-SUPERVISED LEARNING FOR INTERVENTIONAL IMAGE ANALYSIS

(71) Applicant: Siemens Healthineers AG, Forchheim (DE)

(72) Inventors: Dominik Neumann, Erlangen (DE); Saahil Islam, Erlangen (DE); Venkatesh Narasimha Murthy, Hillsborough, NJ (US); Serkan Cimen, West Orange, NJ (US); Florin-Cristian Ghesu, Baiersdorf (DE); Puneet Sharma, Princeton Junction, NJ (US); Dorin Comaniciu, Princeton, NJ (US)

(73) Assignee: Siemens Healthineers AG, Forchheim (DE)

( * ) Notice: Subject to any disclaimer, the term of this patent is extended or adjusted under 35 U.S.C. 154(b) by 263 days.

(21) Appl. No.: 18/419,617

(22) Filed: Jan. 23, 2024

(65) Prior Publication Data

US 2025/0054603 A1     Feb. 13, 2025

Related U.S. Application Data

(60) Provisional application No. 63/518,577, filed on Aug. 10, 2023.

(51) Int. Cl.
*G16H 30/40*        (2018.01)
*G06T 7/00*         (2017.01)
(Continued)

(52) U.S. Cl.
CPC ........... *G16H 30/40* (2018.01); *G06T 7/0012* (2013.01); *G06T 7/11* (2017.01); *G06T 7/20* (2013.01);
(Continued)

(58) Field of Classification Search
CPC ...... G16H 30/40; G16H 30/20; G06T 7/0012; G06T 7/11; G06T 7/20;
(Continued)

(56) References Cited

U.S. PATENT DOCUMENTS

2024/0013509 A1*   1/2024   Cherubini .............. G06V 20/47

OTHER PUBLICATIONS

Gupta, Siamese Masked Autoencoders, arXiv:2305.14344v1 [cs. CV] May 23, 2023 (Year: 2023).*

(Continued)

*Primary Examiner* — Vu Le
*Assistant Examiner* — Lei Zhao

(57) ABSTRACT

Systems and methods for performing one or more medical imaging analysis tasks are provided. A sequence of medical images is received. One or more patches are extracted from each image of the sequence of medical images. Spatio-temporal features are extracted from the one or more extracted patches using a machine learning based encoder network. One or more medical imaging analysis tasks are performed based on the extracted spatio-temporal features. Results of the one or more medical imaging analysis tasks are output. The machine learning based encoder network is trained by receiving a sequence of training medical images. Patches of a first set of images of the sequence of training medical images are masked according to a first masking strategy. Patches of a second set of images of the sequence of training medical images are masked according to a second masking strategy. The machine learning based encoder network is trained to learn a spatio-temporal relationship between the unmasked patches of the first set of images and the second set of images. The machine learning based encoder network is output.

16 Claims, 17 Drawing Sheets

200

(51) Int. Cl.
    *G06T 7/11*           (2017.01)
    *G06T 7/20*           (2017.01)
    *G06V 10/44*         (2022.01)
    *G16H 30/20*         (2018.01)

(52) U.S. Cl.
    CPC ............. *G06V 10/44* (2022.01); *G16H 30/20* (2018.01); *G06T 2207/30021* (2013.01)

(58) Field of Classification Search
    CPC . G06T 2207/30021; G06T 2207/10016; G06T 2207/10121; G06T 2207/20084; G06T 2207/30101; G06V 10/44
    See application file for complete search history.

(56)           References Cited

OTHER PUBLICATIONS

He, Masked Autoencoders Are Scalable Vision Learners, Proceedings of the IEEE/CVF conference on computer vision and pattern recognition, 2022 (Year: 2022).*

Li, RGMIM: Region-Guided Masked Image Modeling for Learning Meaningful Representation from X-Ray Images, arXiv: 2211.00313v4 [cs. CV] May 21, 2023 (Year: 2023).*

Wang, MPS-AMS: Masked Patches Selection and Adaptive Masking Strategy Based Self-Supervised Medical Image Segmentation, InICASSP 2023-2023 IEEE International Conference on Acoustics, Speech and Signal Processing (ICASSP) Jun. 4, 2023 (pp. 1-5) (Year: 2023).*

Yu et al., "Deformable siamese attention networks for visual object tracking," Proceedings of the IEEE/CVF Conference on Computer Vision and Pattern, 2020, pp. 6728-6737.

Zhang et al., "Learn to match: automatic matching network design for visual tracking", Proceedings of the IEEE/CVF International Conference on Computer Vision, 2021, pp. 13339-13348.

Yan et al., "Learning spatio-temporal transformer for visual tracking", Proceedings of the IEEE/CVF International Conference on Computer Vision, 2021, pp. 10448-10457.

Kugarajeevan et al., "Transformers in single object tracking: an experimental survey", IEEE Access, 2023, pp. 80297-80326.

Wang et al., "Transformer meets tracker: Exploiting temporal context for robust visual tracking", Proceedings of the IEEE/CVF Conference on Computer Vision and Pattern Recognition, 2021, pp. 1571-1580.

Chen et al., "Transformer Tracking", Proceedings of the IEEE/CVF Conference on Computer Vision and Pattern Recognition, 2021, pp. 8126-8135.

Wei et al., "Autoregressive visual tracking", Proceedings of the IEEE/CVF Conference on Computer Vision and Pattern Recognition, 2023, pp. 9697-9706.

Vaswani et al., "Attention is all you need", Advances in Neural Information Processing Systems, 2017, pp. 1-15.

Fan et al., "LaSOT: A high-quality benchmark for large-scale singlE object tracking," Proceedings of the IEEE/CVF conference on computer vision and pattern recognition, 2019, pp. 5374-5383.

Kokkinos, "Ubernet: Training a universal convolutional neural network for low-, mid-, and high-level vision using diverse datasets and limited memory", Proceedings of the IEEE Conference on Computer Vision and Pattern Recognition, 2017, pp. 6129-6138.

Wang et al., "Semi-supervised multi-task learning for semantics and depth", Proceedings of the IEEE/CVF Winter Conference on Applications of Computer Vision, 2022, pp. 2505-2514.

Li et al., "Learning without forgetting", arXiv:1606.09282v3, 2017, pp. 1-13.

Kendall et al., "Multi-task learning using uncertainty to weigh losses for scene geometry and semantics", arXiv:1705.07115v1, 2017, pp. 1-13.

Chen et al., "GradNorm: Gradient normalization for adaptive loss balancing in deep multitask networks", arXiv:1711.02257v3, 2018, 10 pgs.

Araki et al., "A comparative approach of four different image registration techniques for quantitative assessment of coronary artery calcium lesions using intravascular ultrasound"; Computer Methods and Programs in Biomedicine, 2014, pp. 1-15.

Bromley et al., "Signature verification using a "Siamese" time delay neural network", Advances in Neural Information Processing Systems, 1993, pp. 737-739.

Cui et al., "Mixformer: End-to-end tracking with iterative mixed attention", Proceedings of the IEEE/CVF Conference on Computer Vision and Pattern Recognition, 2022, 12 pgs.

Dosovitskiy et al., "An image is worth 16×16 words: Transformers for image recognition at scale", arXiv:2010.11929v2, 2021, pp. 1-22.

Facciorusso et al., "Transarterial chemoembolization: Evidences from the literature and applications in hepatocellular carcinoma patients", World Journal of Hepatology, 2009, pp. 1-11.

Gupta et al., "Siamese Masked Autoencoders", arXiv:2305.14344v1, 2023, pp. 1-16.

Li et al., "High performance visual tracking with Siamese region proposal network", In Proceedings of the IEEE conference on computer vision and pattern recognition, 2018, pp. 8971-8980.

Lin et al., "CycleYnet: Semi-supervised Tracking of 3D Anatomical Landmarks", Machine Learning in Medical Imaging, 2020, pp. 593-602.

Lin et al., "Swintrack: A simple and strong baseline for transformer tracking", 36th Conference on Neural Information Processing Systems, 2022, pp. 16743-16754.

Liu et al., "Swin transformer: Hierarchical vision transformer using shifted windows", arXiv:2103.1403v2, 2021, pp. 1-14.

Ma et al., "Dynamic coronary roadmapping via catheter tip tracking in x-ray fluoroscopy with deep learning based Bayesian filtering", Medical Image Analysis, 2020, pp. 1-30.

Odening et al., "ESC working group on cardiac cellular electrophysiology position paper: relevance, opportunities, and limitations of experimental models for cardiac electrophysiology research", Eurospace, 2021, pp. 1795-1814.

Park et al., "What Do Self-Supervised Vision Transformers Learn?", ICLR, 2023, pp. 1-19.

Piayda et al., "Dynamic coronary roadmapping during percutaneous coronary intervention: a feasibility study", European Journal of Medical Research, 2018, pp. 1-7.

Teed et al., "RAFT: Recurrent all-pairs field transforms for optical flow", Proceedings of the 13th International Joint Conference on Artificial Intelligence, 2020.

Tong et al., "VideoMAE: Masked autoencoders are data-efficient learners for self-supervised video pre-training", Advances in Neural Information Processing Systems; 2022, pp. 2-9.

Wang et al., "Image-based device tracking for the co-registration of angiography and intravascular ultrasound images", Medical Image Computing and Computer-Assisted Intervention—MICCAI, 2011, pp. 161-168.

Wang et al., "Image-based co-registration of angiography and intravascular ultrasound images", IEEE Transactions on Medical Imaging, 2013, pp. 2238-2249.

Li et al., "SiamRPN++: Evolution of Siamese visual tracking with very deep networks", arXiv:1812.11703v1, 2018, pp. 1-10.

Demoustier et al., "ConTrack: contextual transformer for device tracking in x-ray," arXiv:2307.07541v1, 2023, pp. 1-10.

Doersch et al., "Unsupervised visual representation learning by context prediction," Proceedings of the IEEE International Conference on Computer Vision, 2015, pp. 1422-1430.

Pathak et al., "Learning features by watching objects move", arXiv:1612.06370v2; 2017, pp. 1-10.

Gidaris et al., "Unsupervised representation learning by predicting image rotations," arXiv:1803.07728v1, 2018, pp. 1-16.

Wu et al., "Unsupervised feature learning via non-parametric instance discrimination," Proceedings of the IEEE Conference on Computer Vision and Pattern Recognition, 2018, pp. 3733-3742.

He et al., "Momentum contrast for unsupervised visual representation Learning," arXiv:1911.05722v3, 2020, pp. 1-12.

Caron et al., "Emerging properties in self-supervised vision transformers", IEEE/CVF International Conference on Computer Vision, 2021, pp. 1-22.

(56) References Cited

OTHER PUBLICATIONS

Chen et al., "A simple framework for contrastive learning of visual representations," International Conference on Machine Learning, 2020, pp. 1-11.

Grill et al., "Bootstrap your own latent—A new approach to self-supervised learning," Advances in Neural Information Processing Systems, 2020, pp. 1-14.

Chen et al., "Exploring simple Siamese representation learning," arXiv:2011.10566v1, 2020, pp. 1-10.

Sermanet et al., "Time-contrastive networks: Self-supervised learning from video", arXiv:1704.06888v3, 2018, pp. 1-15.

Sun et al., "Learning video representations using contrastive bidirectional transformer", arXiv:1906.05743v2, 2019, pp. 1-12.

Han et al., "Video representation learning by dense predictive coding", arXiv:1909.04656v3, 2019, pp. 1-13.

Feichtenhofer et al., "A large-scale study on unsupervised spatiotemporal representation learning", arXiv:2104.14558v1, 2021, pp. 1-16.

Recasens et al., "Broaden your views for self-supervised video learning", Proceedings of the IEEE/CVF International Conference on Computer Vision; 2021, 14 pgs.

Qian et al., "Spatiotemporal contrastive video representation learning", Proceedings of the IEEE/CVF Conference on Computer Vision and Pattern Recognition, 2021, 11 pgs.

Devlin et al., "BERT: Pre-training of deep bidirectional transformers for language understanding", arXiv:1810.04805v2, 2019, 16 pgs.

Feichtenhofer et al., "Masked autoencoders as spatiotemporal learners", arXiv:2205.09113v2, 2022, 18 pgs.

Chen et al., "Masked autoencoders are scalable vision learners", arXiv:2111.06377v3, 2021, pp. 1-14.

Bao et al., "Beit: BERT pre-training of image transformers", arXiv:2106.08254v2, 2022, 18 pgs.

Xie et al., "SimMIM: A simple framework for masked image modeling", Proceedings of the IEEE/CVF Conference on Computer Vision and Pattern Recognition, 2022, 13 pgs.

Fan et al., "Siamese cascaded region proposal networks for real-time visual tracking", Proceedings of the IEEE/CVF Conference on Computer Vision and Pattern recognition, 2019, pp. 7952-7961.

Zhu et al., "Distractor-aware siamese networks for visual object tracking", Proceedings of the European Conference on Computer Vision, 2018, pp. 1-17.

Fan et al., "CRACT: Cascaded regression-align-classification for robust tracking", IEEE/RSJ International Conference on Intelligent Robots and Systems, 2021, 8 pgs.

* cited by examiner

Figure 1:
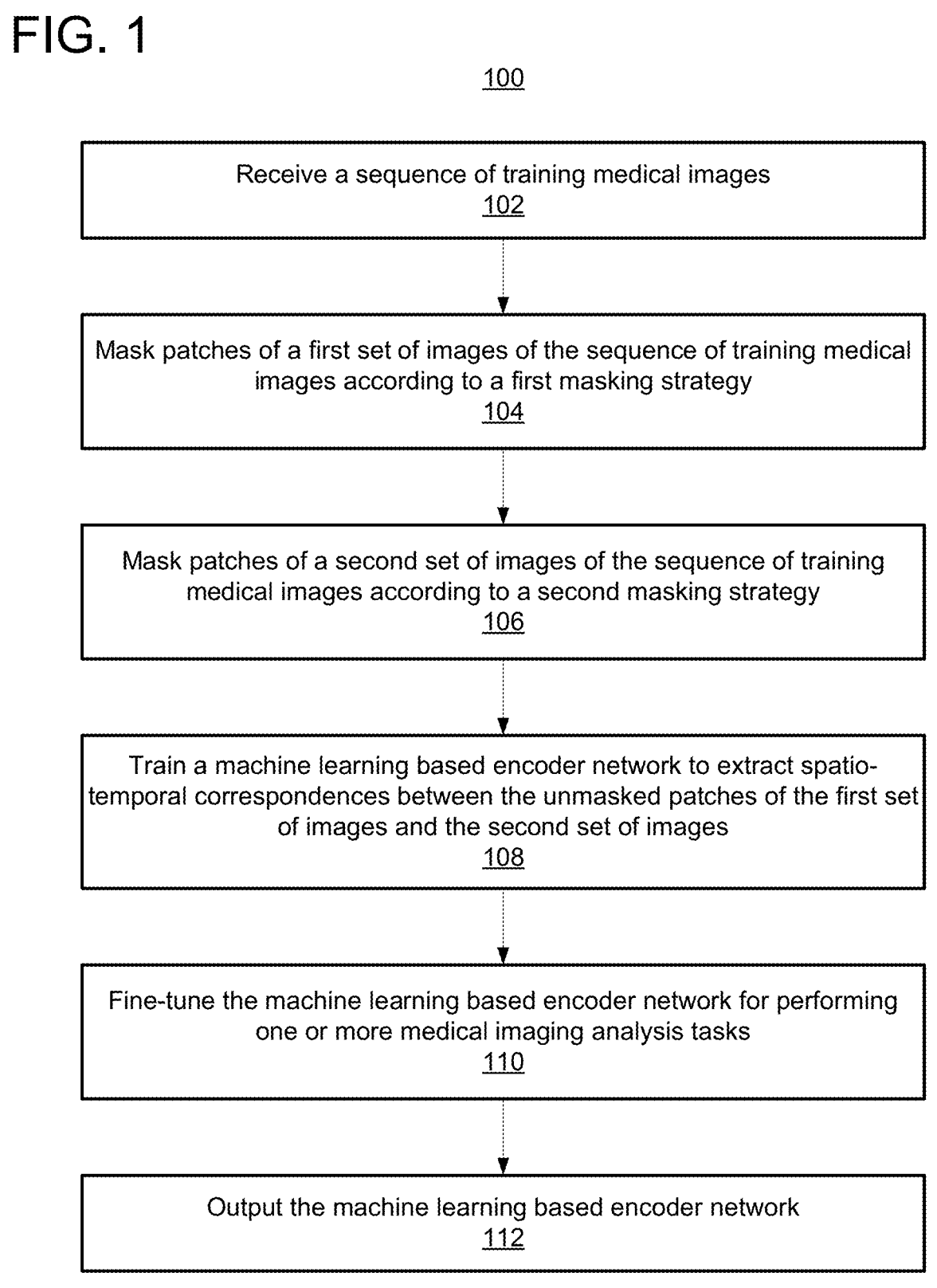

Receive a sequence of training medical images
102

Mask patches of a first set of images of the sequence of training medical images according to a first masking strategy
104

Mask patches of a second set of images of the sequence of training medical images according to a second masking strategy
106

Train a machine learning based encoder network to extract spatio-temporal correspondences between the unmasked patches of the first set of images and the second set of images
108

Fine-tune the machine learning based encoder network for performing one or more medical imaging analysis tasks
110

Output the machine learning based encoder network
112

Figure 4:
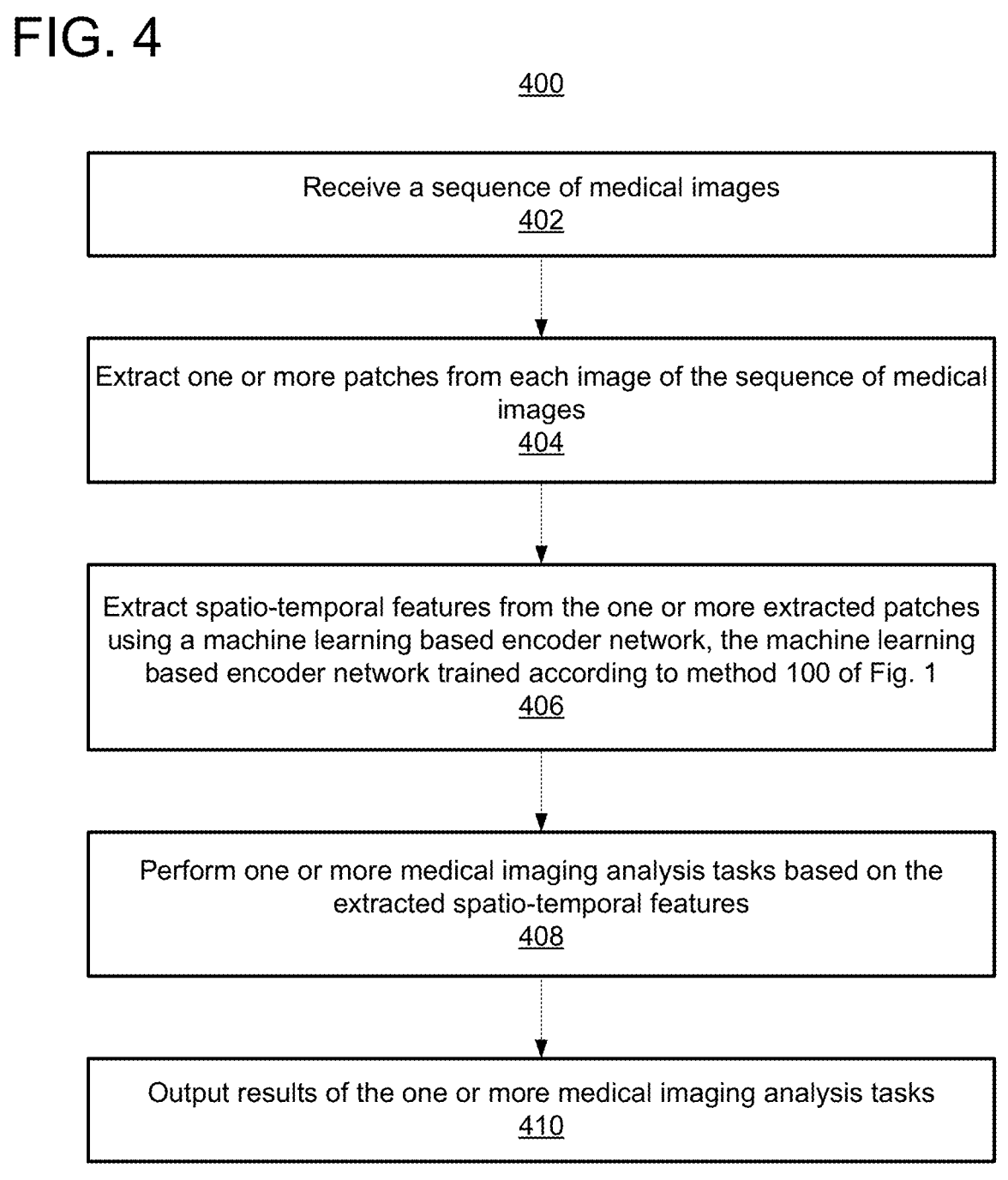

Receive a sequence of medical images
402

Extract one or more patches from each image of the sequence of medical images
404

Extract spatio-temporal features from the one or more extracted patches using a machine learning based encoder network, the machine learning based encoder network trained according to method 100 of Fig. 1
406

Perform one or more medical imaging analysis tasks based on the extracted spatio-temporal features
408

Output results of the one or more medical imaging analysis tasks
410

502 504 506

Fluoroscopy Angiography Devices

| Models | Median (mm) ↓ | Mean (mm) ↓ | Std (mm) ↓ | 95 Percentile (mm) ↓ | Max (mm) ↓ | Speed (fps) ↑ |
|---|---|---|---|---|---|---|
| SiameseRPN[34] | 7.13 | 9.01 | 6.81 | 22.37 | 46.23 | 18 |
| STARK[41] | 2.65 | 4.14 | 4.93 | 9.24 | 31.34 | 22 |
| MixFormer[42] | 2.68 | 5.15 | 7.1 | 19.20 | 49.29 | 20 |
| Cycle Ynet[10] | 1.96 | 2.68 | 2.4 | 6.75 | 21.04 | 109 |
| ConTrack-base[11] | 1.13 | 2.17 | 3.75 | 6.34 | 31.35 | 21 |
| ConTrack-mtmt[11] | 1.12 | 1.97 | 3.61 | 5.53 | 30.37 | 19 |
| ConTrack-optim[11] | 1.08 | 1.63 | 1.7 | 5.18 | 13.32 | 12 |
| FIMAE | 1.02 | 1.44 | 1.35 | 3.52 | 10.23 | 42 |

FIG. 7
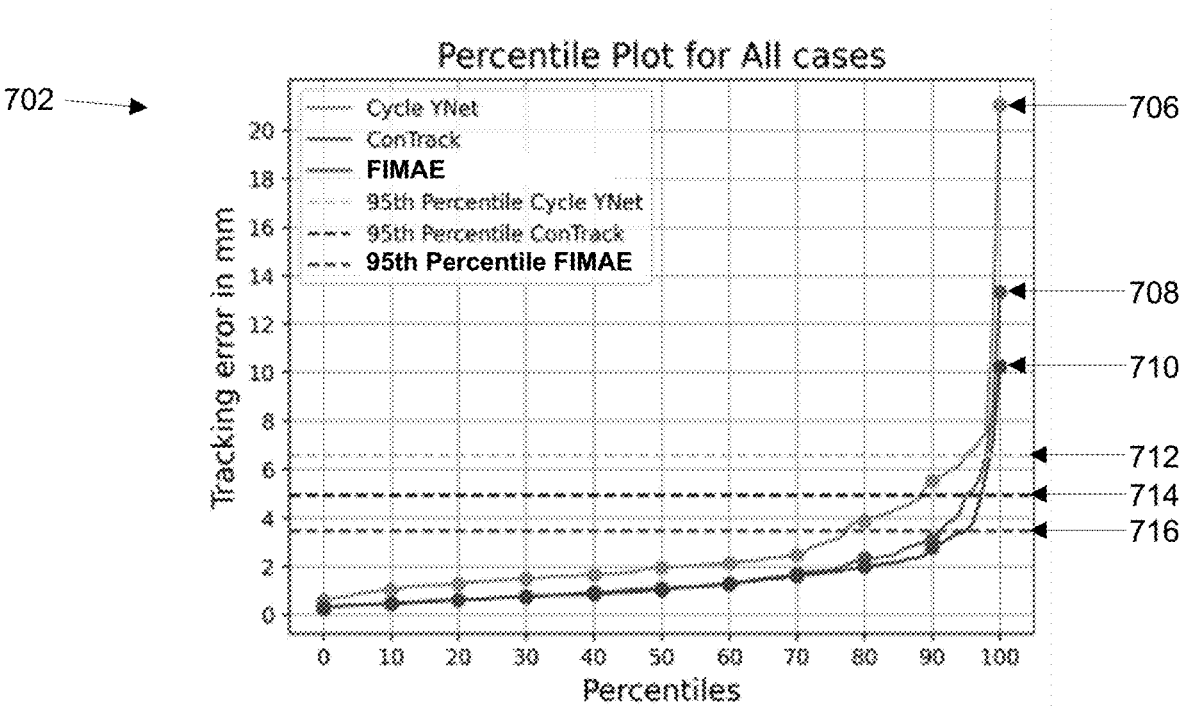
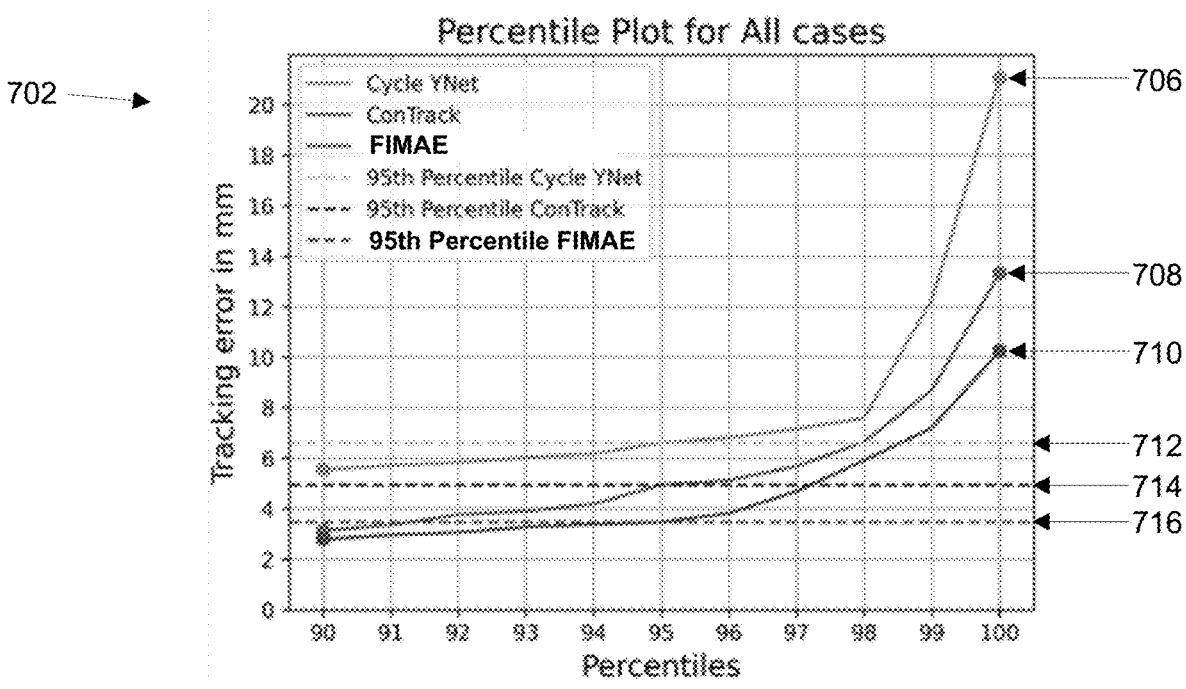

| Pretraining strategy | Median (mm) | Mean (mm) | Std (mm) | Max (mm) |
|---|---|---|---|---|
| VideoMAE-Kinetics | 1.93 | 3.67 | 4.95 | 36.99 |
| VideoMAE ($\mathcal{D}_u$) | 1.48 | 2.75 | 4.64 | 53.26 |
| SiamMAE ($\mathcal{D}_u$) | 1.54 | 2.79 | 3.44 | 23.76 |
| FIMAE ($\mathcal{D}_u$) | 1.02 | 1.44 | 1.35 | 10.23 |

FIG. 11
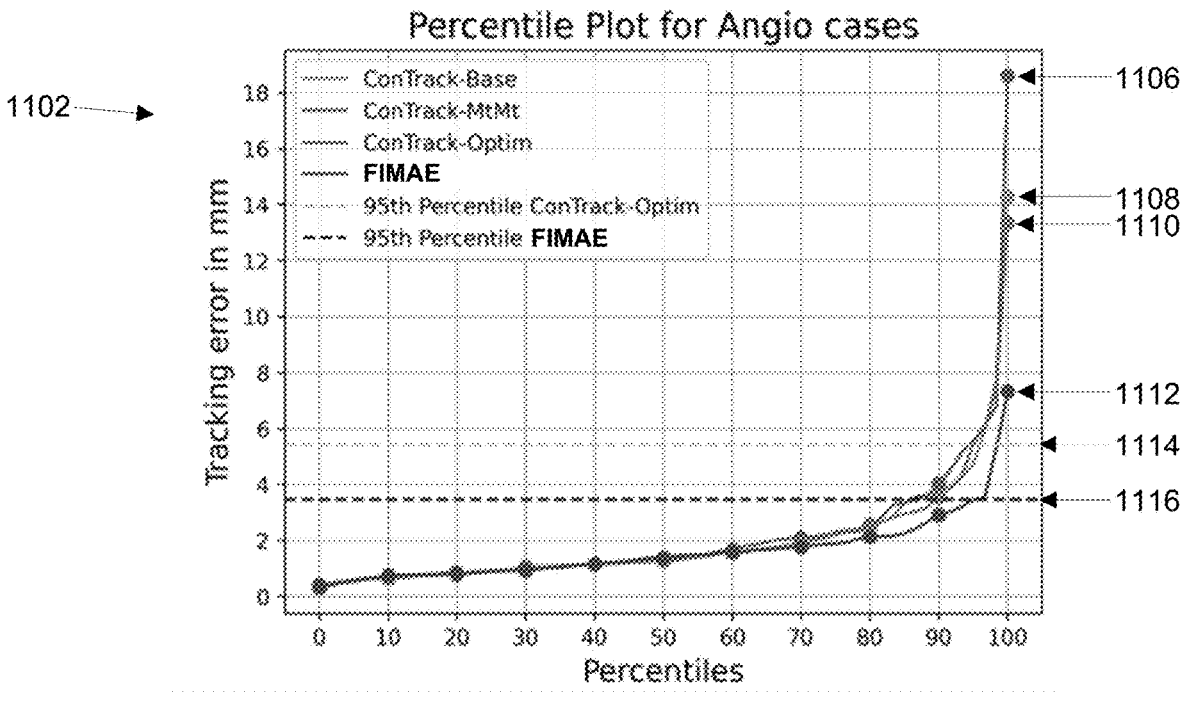
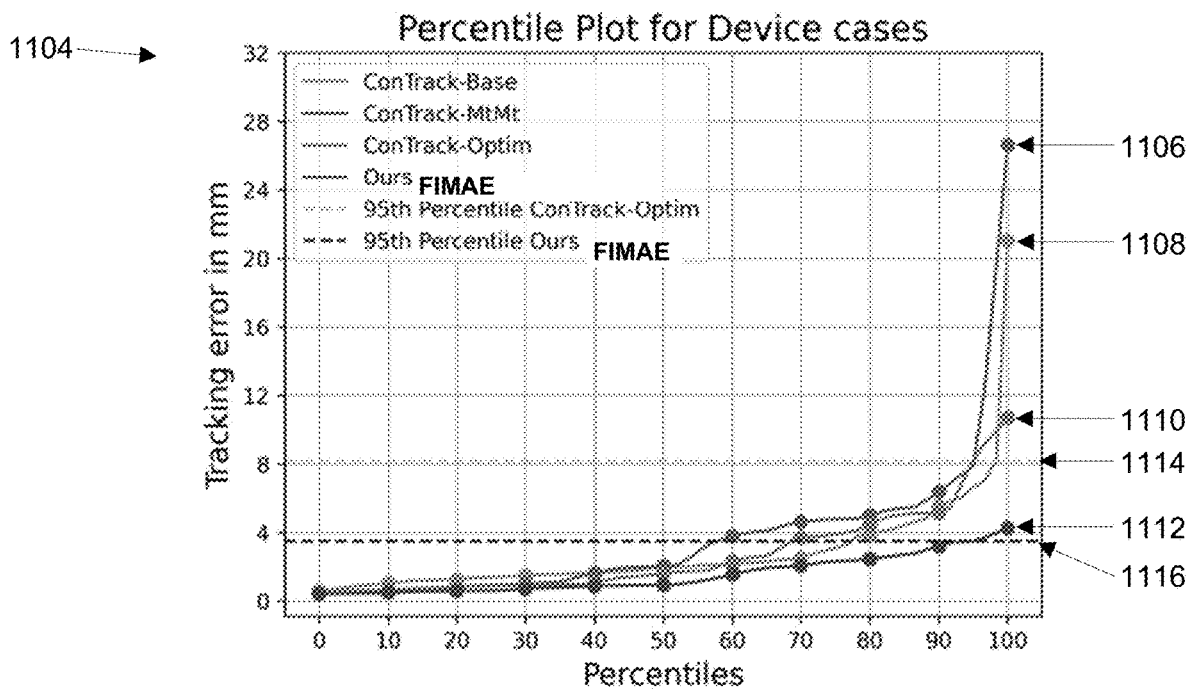

| Positional Encoding | Median | Mean | Std | Max |
|---|---|---|---|---|
| Naive | 1.47 | 2.51 | 3.43 | 36.24 |
| Learnable | 1.37 | 1.86 | 1.54 | 11.22 |
| Frame-aware (FIMAE) | 1.02 | 1.44 | 1.35 | 10.23 |

| Frame Masking ratio | Median | Mean | Std | Max |
|---|---|---|---|---|
| 95% | 1.09 | 1.47 | 1.24 | 10.34 |
| 98% | 1.02 | 1.44 | 1.35 | 10.23 |
| 100% | 1.08 | 1.78 | 2.09 | 15.12 |

SELF-SUPERVISED LEARNING FOR INTERVENTIONAL IMAGE ANALYSIS

CROSS-REFERENCE TO RELATED APPLICATIONS

This application claims the benefit of U.S. Provisional Application No. 63/518,577, filed Aug. 10, 2023, the disclosure of which is herein incorporated by reference in its entirety.

TECHNICAL FIELD

The present invention relates generally to AI/ML (artificial intelligence/machine learning) based systems and methods for medical imaging analysis, and in particular to self-supervised learning for interventional image analysis.

BACKGROUND

AI/ML techniques have recently been proposed for performing various medical imaging analysis tasks. Conventional AI/ML systems for medical imaging analysis typically involves complex processing pipelines and multiple hand-crafted AI/ML modules, particularly in the domain of invasive cardiac interventions. Such conventional AI/ML systems are often designed as a complex concatenation of specialized single-purpose AI/ML components. Each AI/ML component is typically trained on its own database of manually curated and annotated images and is unaware of features and representations learned by the other AI/ML components, even if they could benefit the task at hand. Further, such conventional AI/ML systems are therefore susceptible to intermediate errors and error accumulation.

BRIEF SUMMARY OF THE INVENTION

In accordance with one or more embodiments, systems and methods for performing one or more medical imaging analysis tasks are provided. A sequence of medical images is received. One or more patches are extracted from each image of the sequence of medical images. Spatio-temporal features are extracted from the one or more extracted patches using a machine learning based encoder network. One or more medical imaging analysis tasks are performed based on the extracted spatio-temporal features. Results of the one or more medical imaging analysis tasks are output. The machine learning based encoder network is trained by receiving a sequence of training medical images. Patches of a first set of images of the sequence of training medical images are masked according to a first masking strategy. Patches of a second set of images of the sequence of training medical images are masked according to a second masking strategy. The machine learning based encoder network is trained to learn a spatio-temporal relationship between the unmasked patches of the first set of images and the second set of images. The machine learning based encoder network is output.

In one embodiment, the spatio-temporal features represent spatio-temporal correspondences between the one or more patches.

In one embodiment, random patches at a same spatial location are masked across the first set of images and random patches are masked in each of the second set of images.

In one embodiment, the machine learning based encoder network is jointly trained with a machine learning based decoder network for reconstructing the patches of the first set of images and the second set of images.

In one embodiment, the first set of images comprises alternating images of the sequence of training medical images and the second set of images comprises the remaining images of the sequence of training medical images.

In one embodiment, the one or more patches are encoded with positional encodings determined during the training of the machine learning based encoder network.

In one embodiment, the one or more medical imaging analysis tasks comprises one or more of tracking a tip of a catheter or tracking a catheter in a patient.

In accordance with one embodiment, systems and methods for training a machine learning based encoder network are provided. A sequence of training medical images is received. Patches of a first set of images of the sequence of training medical images are masked according to a first masking strategy. Patches of a second set of images of the sequence of training medical images are masked according to a second masking strategy. A machine learning based encoder network is trained to learn a spatio-temporal relationship between the unmasked patches of the first set of images and the second set of images. The machine learning based encoder network is output.

In one embodiment, random patches at a same spatial location are masked across the first set of images and random patches are masked in each of the second set of images.

In one embodiment, the machine learning based encoder network is jointly trained with a machine learning based decoder network for reconstructing the patches of the first set of images and the second set of images.

In one embodiment, the first set of images comprises alternating images of the sequence of training medical images and the second set of images comprises the remaining images of the sequence of training medical images.

These and other advantages of the invention will be apparent to those of ordinary skill in the art by reference to the following detailed description and the accompanying drawings.

BRIEF DESCRIPTION OF THE DRAWINGS

FIG. 1 shows a method for training a machine learning based encoder network, in accordance with one or more embodiments;

FIG. 4 shows a method for performing one or more medical imaging analysis tasks using a trained machine learning based encoder network, in accordance with one or more embodiments;

FIG. 6 shows a table comparing the FIMAE (frame interpolation masked autoencoder) approach, implementing embodiments described herein, with conventional approaches;

FIG. 7 shows graphs of percentile plots tracking error;

FIG. 8 shows a table comparing the effect of pretraining strategies on the performance of catheter tip tracking;

FIG. 11 shows percentile plots tracking error for angio cases and for device cases;

FIG. 13 shows a table comparing positional encoding strategies on downstream task performance for the naïve strategy, the learnable strategy, and the frame-aware (FI-MAE) strategy;

FIG. 14 shows a table of tracking performance of the FIMAE approach trained with different intermediate frame masking ratios;

DETAILED DESCRIPTION

The present invention generally relates to methods and systems for self-supervised learning for interventional image analysis. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system. Further, reference herein to pixels of an image may refer equally to voxels of an image and vice versa.

Embodiments described herein provide for a frame interpolation masked autoencoder approach for training a machine learning based encoder network for encoding a sequence of medical images into spatio-temporal features for performing a medical imaging analysis task. The encoder network is pre-trained via self-supervised learning using spatio-temporal features extracted from a dataset of unannotated training medical images to learn inter-frame correspondences over a large number of images. The pre-trained encoder network is then fine-tuned with a machine learning based decoder network via supervised learning using a dataset of annotated training medical images for performing a downstream medical imaging analysis task. The encoder network and decoder network are trained during a prior offline or training stage, as described with respect to, e.g., FIGS. 1 and 2. Once trained, the trained encoder network and decoder network are applied during an online or inference stage, as described with respect to, e.g., FIG. 4.

Advantageously, the pre-trained encoder network may be fine-tuned with the decoder network to perform a plurality of medical imaging analysis tasks using multitask learning, thereby reducing the complexity of AI/ML systems by inferring outputs of each medical imaging analysis task concurrently with the same pre-trained encoder network. Embodiments described herein reduce the memory footprint of the AI/ML systems and the overall inference time. Multitask learning further generates consistent results for all medical imaging analysis tasks by leveraging information of related tasks and providing regularization across tasks.

Figure 2:
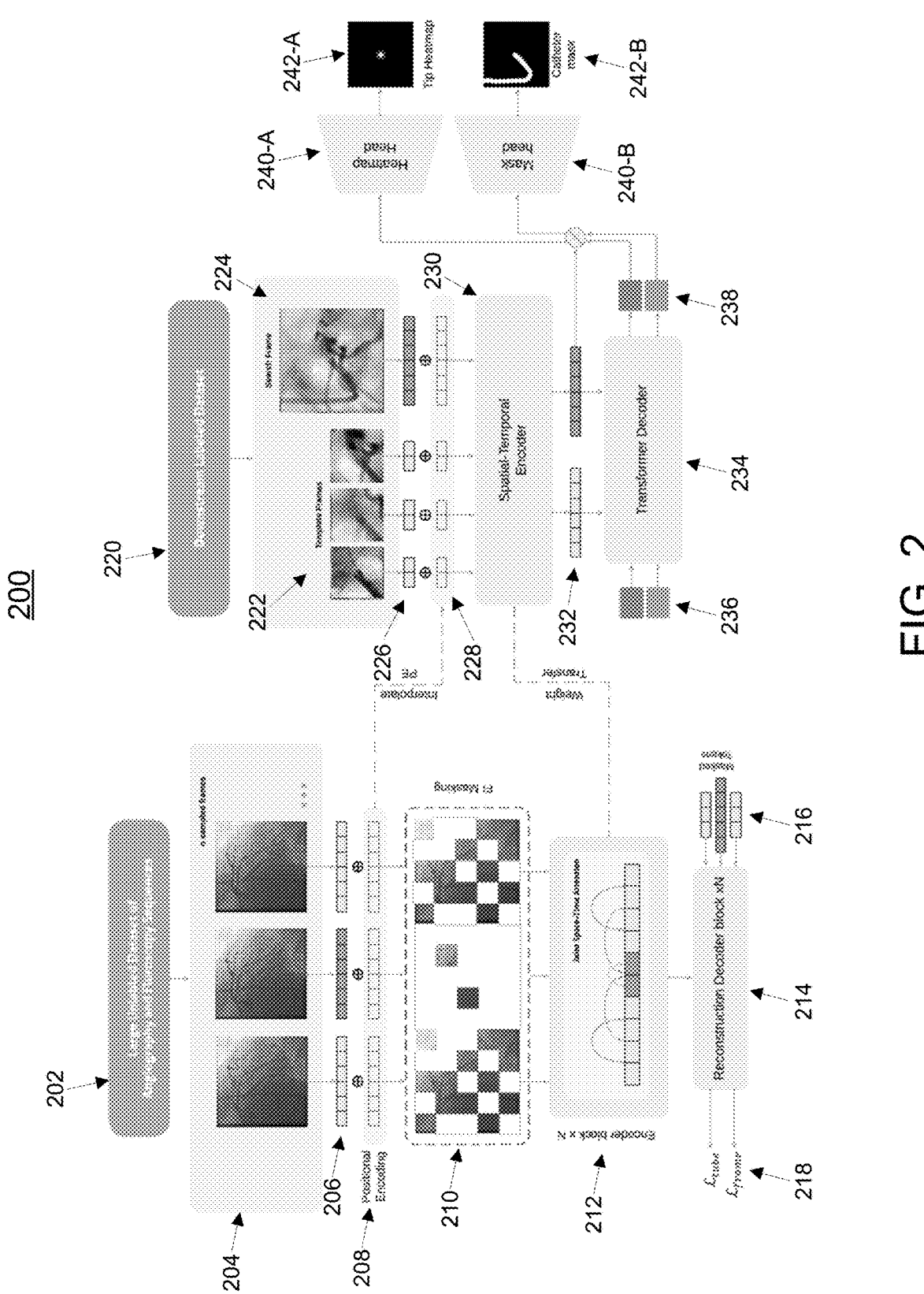
FIG. 2 shows a workflow for training a machine learning based encoder network, in accordance with one or more embodiments.

FIG. 1 shows a method 100 for training a machine learning based encoder network, in accordance with one or more embodiments. The steps of method 100 may be performed by one or more suitable computing devices, such as, e.g., computer 1702 of FIG. 17. FIG. 2 shows a workflow 200 for training a machine learning based encoder network, in accordance with one or more embodiments. The steps of method 100 of FIG. 1 and workflow 200 of FIG. 2 are performed during a prior offline or training stage for training machine learning based encoder and decoder networks. Once trained, the trained encoder and decoder networks may be applied, e.g., according to method 400 of FIG. 4. FIG. 1 and FIG. 2 will be described together.

At step 102 of FIG. 1, a sequence of training medical images is received. The sequence of training medical images is a series of two or more images or frames depicting a same anatomical object of interest of a patient taken at different times and/or under different conditions. The anatomical object of interest may be, for example, an organ, a vessel, a bone, a tumor or other abnormality, or any other anatomical object of interest of the patient. The images of the sequence of training medical images are unannotated training medical images. The sequence of training medical images is part of an unannotated dataset of sequences of training medical images. In one example, as shown in workflow 200 of FIG. 2, the sequence of training medical images is a sequence of large unlabeled dataset of angiography and fluoroscopy sequences 202.

In one embodiment, the sequence of training medical images comprises x-ray images. For example, the sequence of training medical images may be fluoroscopy images acquired during an angiography of a patient. However, the sequence of training medical images may be of any other suitable modality, such as, e.g., CT (computed tomography), MRI (magnetic resonance imaging), US (ultrasound), or any other medical imaging modality or combinations of medical imaging modalities. The images of the sequence of training medical images may be 2D (two dimensional) images and/or 3D (three dimensional) volumes.

Figure 17:
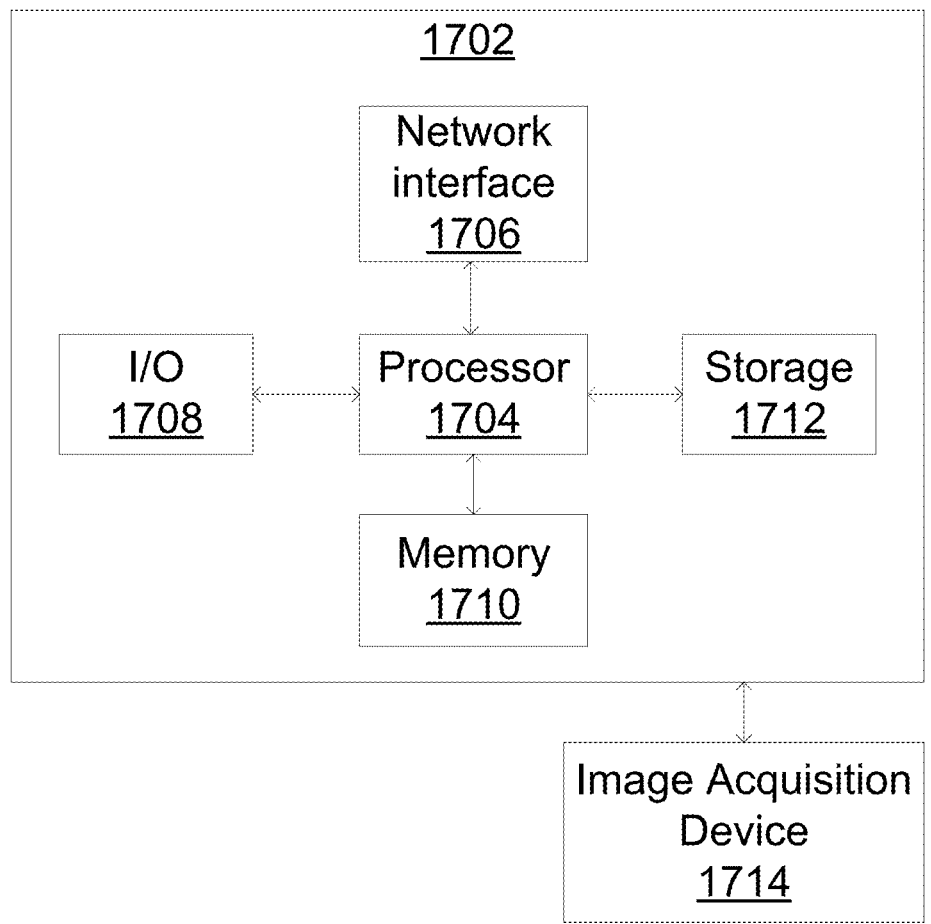
FIG. 17 shows a high-level block diagram of a computer that may be used to implement one or more embodiments.

The sequence of training medical images may be received, for example, directly from an image acquisition device (image acquisition device 1714 of FIG. 17) as the sequence of training medical images is acquired, by loading a previously acquired sequence of training medical images from a storage or memory of a computer system (e.g., memory 1710 or storage 1712 of computer 1702 of FIG. 17), or from a remote computer system (e.g., computer 1702 of FIG. 17).

Formally, unlabeled dataset $\mathcal{D}_u$ comprises sequence $S_k \in \mathcal{D}_u$, $\forall k > 0$ having n images, where $S_{k,n} = [I_1, I_2, \ldots, I_n]$. All images n are randomly cropped to a size of (h, w)=384×384 pixels on a sequence level (i.e., the same crop is applied to each image of the sequence of training medical images). Each input of size (h, w) is spatially encoded into $$n \times \frac{h}{16} \times \frac{w}{16}$$

tokens of dimension $D_m$ with no temporal down sampling.

At step 104 of FIG. 1, patches of a first set of images of the sequence of training medical images are masked according to a first masking strategy and, at step 106 of FIG. 1, patches of a second set of images of the sequence of training medical images are masked according to a second masking strategy. In one example, as shown in workflow 200 of FIG.

2, patches 206 of images 204 are masked 210. Patches 206 are encoded (e.g., concatenated) with a positional encoding 208 representing the relative position of patches 206 with image 204.

The first set of images and the second set of images may be sampled from the sequence of unannotated training medical images according to any suitable approach. In one embodiment, alternating images (i.e., every other image) are sampled from the sequence of unannotated training medical images to generate the first set of images and the remaining, intermediate images are sampled from the sequence of unannotated training medical images to generate the second set of images.

The first and second masking strategies are selected to capture fine spatial and temporal correspondences between images of the sequence. In one embodiment, the first masking strategy is tube masking and the second sampling strategy is frame masking. Tube masking refers to randomly masking patches at the same spatial location across all images (e.g., of the first set of images). Frame masking refers to randomly masking patches in each of the images (e.g., of the second set of images). Tube masking and frame masking are illustratively shown in FIG. 3.

Figure 3:
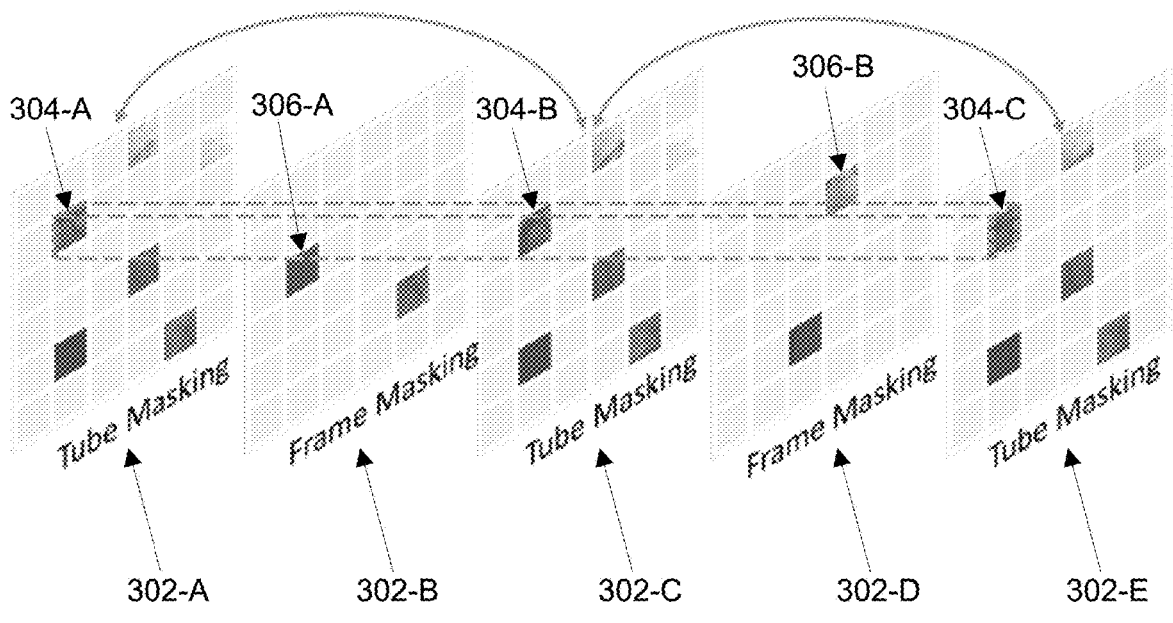
FIG. 3 shows a workflow for tube-frame masking, in accordance with one or more embodiments.

FIG. 3 shows a workflow 300 for tube-frame masking, in accordance with one or more embodiments. As shown in workflow 300, a sequence of training medical images comprises images 302-A, 302-B, 302-C, 302-D, and 302-E. Alternating images 302-A, 302-C, and 302-E are sampled from the sequence to generate a first set of images and the remaining, intermediate images 302-B and 302-D are sampled from the sequence to generate the second set of images. Images 302-A, 302-C, and 302-E are masked according to a tube masking strategy, such that patches 304-A, 304-B, and 304-C at the same spatial location across images 302-A, 302-C, and 302-E are masked. Images 302-B and 302-D are masked according to a frame masking strategy, such that random patches 306-A and 306-B of images 302-B and 302-D are masked. In one embodiment, the tube masking is performed with a ratio of 75% and the frame masking is performed with a ratio of 98%, where such ratios refer to the amount of patches that will be masked/removed. However, the tube masking and frame masking may be performed according to any suitable ratio.

Referring back to steps 104 and 106 of FIG. 1, the first and second masking strategies are based on frame interpolation. The frame interpolation task is defined in Equation (1) as a sum of forward warping and backward warping of any two neighboring frames (indexed by t>0) as follows:

$$I_{t+1} = \tau_{\theta 1}(I_t) + \tau_{\theta 2}(I_{t+2}) \qquad (1)$$

where $\tau_{\theta 1}$ denotes the forward warping operator and $\tau_{\theta 2}$ denotes the backward warping operator, respectively parameterized by θ1 and θ2. Equation (1) is reformulated to a learning problem, seeking to optimize the parameters θ1 and θ2 of a deep neural network to learn a combined warping operator F as shown in Equation (2):

$$I_{t+1} = F_0(I_t, I_{t+2}) \qquad (2)$$

Let $p_t \in \Omega_{tube}$ be the token indices of the tube masked tokens from image t, where $\Omega_{tube}$ denotes the set of all tube masked token indices. Similarly, let $q_t \in \Omega_{frame}$ be the token indices of the frame masked tokens from image t in all randomly frame masked token indices, where $\Omega_{frame}$ denotes the set of all frame masked token indices. Let $p'_t \in \Omega'_{tube}$ and $q'_t \in \Omega'_{frame}$ be the set of remaining visible token indices. Combining tube and frame masking strategies results in the following reconstruction objective in Equation (3) for any three given images of the sequence of training medical images:

$$I_t, I_{t+1}, I_{t+2} = F_0(I_t(p'_t), I_{t+1}(q'_{t+1}), I_{t+2}(p'_{t+2})) \qquad (3)$$

where 0<t<n−1 denotes the index of an arbitrary image from the sampled sequence and $I_t(p'_t)$ denotes the visible patches of image $I_t$ with tube/frame masking applied. The three image objective of Equation (3) can be generalized to all n images.

At step 108 of FIG. 1, a machine learning based encoder network is trained to extract spatio-temporal correspondences between the unmasked patches of the first set of images and the second set of images. In one embodiment, the encoder network is jointly trained with a machine learning based decoder network for reconstructing the first set of images and the second set of images. In one example, as shown in workflow 200 of FIG. 2, the encoder network is encoder 212 and the decoder network is decoder 214.

The encoder network and decoder network may be implemented according to any suitable machine learning based architecture. In one embodiment, the encoder network is a ViT (vision transformer) encoder and the decoder network is a transformer based decoder. The encoder network receives as input the unmasked patches of the first set of images and the second set of images and generates as output spatio-temporal features. The spatio-temporal features are low-level latent features or embeddings representing the unmasked patches. The encoder network adopts a joint space-time attention mechanism. That is, each token for image t is projected and flattened into an $D_m$-dimensional vector query (q), key (k), and value (v) embedding: ($q_t$, $k_t$, $v_t$). The joint space-time attention mechanism is based on the concatenated vectors of Equation (4):

$$\text{Attention}(Q, K, V) = \textit{soft}\max\left(\frac{QK^T}{\sqrt{d}}\right)V \qquad (4)$$

where the variables (QK,V) are defined as Q=Concat($q_1$, $q_2$, . . . , $q_n$), K=Concat($k_1$, $k_2$, . . . , $k_n$), and V=Concat($v_1$, $v_2$, . . . , $v_n$) for n sampled consecutive images of the sequence and concat is the concatenation operation.

The spatio-temporal features representing the encoded visible (unmasked) patches are then combined (e.g., concatenated) with learnable masked tokens. The decoder network receives as input the spatio-temporal features combined with the learnable masked tokens and generates as output reconstructed images or patches of the initially masked patches. The decoder network incorporates additional positional encodings to ensure the correct positions of the masked and unmasked patches as per the original images. In one example, as shown in workflow 200 of FIG. 2, decoder 214 receives as input the spatio-temporal features generated by encoder 212 combined with masked tokens 216 and generates as output reconstructed patches. Masked tokens 216 are learnable tokens that are initialized randomly. Masked tokens 216 correspond to the tokens that were initially masked before being fed into the network. During training, the tokens attend to the visible encoded tokens and learn to reconstruct the masked patches.

The encoder network and decoder network are jointly trained using a weighted MSE (mean squared error) loss $\mathcal{L} = \mathcal{L}_{tube} + \gamma \mathcal{L}_{frame}$ between the masked tokens and the reconstructed patches in the pixel space based on the masking strategy, where $\gamma$ is the weighting factor. In one example, as shown in workflow 200 of FIG. 2, encoder 212 and decoder 214 are jointly trained according to $\mathcal{L}_{tube}$ and $\mathcal{L}_{frame}$ losses 218. Losses $\mathcal{L}_{tube}$ and $\mathcal{L}_{frame}$ are defined in Equations (5) and (6) as follows:

$$\mathcal{L}_{tube} = \frac{1}{|\Omega_{tube}|} \sum_{t=1}^{n} \sum_{p_t \in \Omega_{tube}} \left\| I_t(p_t) - \hat{I}_t(p_t) \right\|^2 \tag{5}$$

$$\mathcal{L}_{frame} = \frac{1}{|\Omega_{frame}|} \sum_{t=1}^{n} \sum_{q_t \in \Omega_{frame}} \left\| I_t(q_t) - \hat{I}_t(q_t) \right\|^2 \tag{6}$$

where I is the input image and $\hat{I}_t$ is the reconstructed image. The weighted loss for reconstruction is used to compensate for the imbalance between low masked images (less reconstruction tokens) and highly masked images (more reconstruction tokens). The variable $\gamma$ is defined as the ratio of the number of $\Omega_{tube}$ tokens and the number of $\Omega_{frame}$ tokens.

At step 110 of FIG. 1, the machine learning based encoder network is fine-tuned for performing one or more medical imaging analysis tasks. The one or more medical imaging analysis tasks may comprise any suitable medical imaging analysis task.

In one embodiment, as shown in workflow 200 of FIG. 2, the one or more medical imaging analysis tasks comprise medical device tracking in a patient (e.g., for tracking a catheter or a catheter tip). The goal is to track the location $\hat{y}_t = (u_t, v_t)$ of the tip of the catheter at any time t, t>0 given a sequence of images $$\{I_t\}_{t=1}^{n}$$

with a known initial location of the catheter tip $y_1 = (u_1, v_1)$ from labeled dataset $D_l$ 220. The sequences $S_k \in \mathcal{D}_l$, $\forall k > 0$ have a few annotated labels, $S_{k,n} = [(I_1, y_1), I_2, \ldots, (I_7, y_7), I_8, \ldots]$. To identify the location of the tip of the catheter at the current search image, three template images 222 are cropped from the first annotated image and the previous two annotated images of the sequence, respectively. The current image is used for the template images if no previously annotated images are available. During inference, the last two template images are dynamically updated, while the first is kept intact.

Three template images 222 and a search image 224 are utilized as four distinct inputs. Template images 222 are past images/frames while search image 224 is a current image/frame on which the medical imaging analysis task is to be performed. Each patch 226 extracted from template images 222 and search image 224 is respectively encoded (e.g., concatenated) with positional encodings 228 interpolated from positional encodings 208 determined during the pre-training setup to ensure the spatial-temporal encoder 230 distinguishes each template and search image as distinct images. In particular, each of template images 222 and search image 224 corresponds to the positions of center crops of individual frames in the pretraining setup. Therefore, encoder 230 receives as input Concat($te_1$, $te_2$, $te_3$, $f_{se}$), where $te_{1,2,3}$ and se are the template images and search image respectively and generates as output spatio-temporal features 232 $f_c$ = Concat($f_{te1}$, $f_{te2}$, $f_{te3}$, $f_{se}$) of the template images 222 and search image 224. Encoder 230 is trained to extract fine inter-frame correspondences between the template images 222 and search image 224. Template images 222 provide cues about the change of appearance of the concerned point to track. Encoder 230 tries to understand this change of appearance and match it with the search image 224 for proper detection. Hence, this results in a joint feature extract and feature matching between the template frames 222 and the search frame 224. It should be understood that while encoder 212 and encoder 230 are separately shown in workflow 200 for illustrative purposes, encoder 230 and encoder 212 is the same encoder.

Encoder 230 is jointly trained with decoder 234 for performing the one or more medical imaging analysis tasks. Decoder 234 may be any suitable machine learning based decoder network. In one embodiment, decoder 234 is a transformer based decoder. It should be understood that decoder 234 and decoder 214 are separate decoders. Spatio-temporal features $f_c$ 232 are first projected to a lower dimension $d_m$. Decoder 234 uses two learnable query tokens ($h_d$, $m_d$) 236 for heatmap head 240-A and mask head 240-B respectively. Query tokens 236 are learnable queries initialized randomly. Each layer of decoder 234 first computes attention on query tokens 236 according to Equation (4), followed by cross-attention with encoded spatio-temporal features $f_c$ 232 to generate resulting query tokens 238, where key and value embeddings are computed by projecting spatio-temporal features $f_c$ 232 to dimension $d_m$. The resulting query tokens 238 are the same tokens as query tokens 236 after attending to the encoded spatio-temporal features $f_c$ 232. Two tokens are illustratively shown for query tokens 236 and for resulting query tokens 238 corresponding to the medical imaging analysis tasks (e.g., catheter tip detection and catheter mask predictions, as shown in FIG. 2). The resulting query tokens 238 are then correlated with the spatio-temporal features $f_c$ 232, unflattened, and passed though heads 240-A and 240-B to respectively generate tip heatmap 242-A and catheter mask 242-B. Heads 240-A and 240-B may be implemented as CNN (convolutional neural networks) or any other suitable machine learning based architecture. Heatmap 242-A and catheter mask 242-B are obtained according to Equations (7) and (8):

$$P_h = Conv_h \left( \text{Unflatten} \left( corr(f_{se}, h_d) \right) \right) \tag{7}$$

$$P_m = Conv_m \left( \text{Unflatten} \left( corr(f_{se}, m_d) \right) \right) \tag{8}$$

where $P_h$ and $P_m$ refer to the predicted heatmap of the catheter tip and the predicted mask of the catheter respectively The final tip coordinates are obtained by $\hat{y} = \max(P_h)$. Encoder 230, decoder 234, and heads 240-A and 240-B are jointly trained according to a soft dice loss $\mathcal{L}_{dice} = \mathcal{L}_h + \lambda \mathcal{L}_m$ given by Equations (9) and (10):

$$\mathcal{L}_h = \frac{2 * \sum G_h * P_h}{\sum G_h^2 + \sum P_h^2 + \epsilon} \tag{9}$$

-continued $$\mathcal{L}_h = \begin{cases} \dfrac{2 * \sum G_m * P_m}{\sum G_m^2 + \sum P_m^2 + \in} & \text{if } G_m \text{ exists} \\ 0 & \text{otherwise} \end{cases} \quad (10)$$

where G represents ground truth labels and A is the weight for weighting mask loss.

At step 112 of FIG. 1, the machine learning based encoder network and/or the machine learning based decoder network (trained at step 110 of FIG. 1) are output. For example, the machine learning based encoder network and/or the machine learning based decoder network can be output by storing the machine learning based encoder network and/or the machine learning based decoder network on a memory or storage of a computer system (e.g., memory 1710 or storage 1712 of computer 1702 of FIG. 17) or by transmitting the machine learning based encoder network and/or the machine learning based decoder network to a remote computer system (e.g., computer 1702 of FIG. 17).

FIG. 4 shows a method 400 for performing one or more medical imaging analysis tasks using a trained machine learning based encoder network, in accordance with one or more embodiments. The steps of method 100 may be performed by one or more suitable computing devices, such as, e.g., computer 1702 of FIG. 17. The steps of method 100 are performed during an online or inference stage using a trained encoder and decoder networks, which may be trained according to, e.g., method 100 of FIG. 1 or workflow 200 of FIG. 2.

At step 402 of FIG. 4, a sequence of medical images is received. The sequence of medical images is a series of two or more images depicting a same anatomical object of interest of a patient taken at different times and/or under different conditions. In one embodiment, the sequence of medical images comprises one or more template images and a search image. The sequence of medical images may be of any suitable modality, such as, e.g., x-ray, CT, MRI, US, or any other medical imaging modality or combinations of medical imaging modalities. The images of the sequence of medical images may be 2D images and/or 3D volumes.

The sequence of medical images may be received directly, for example, from an image acquisition device (image acquisition device 1714 of FIG. 17) as the sequence of medical images is acquired, by loading a previously acquired sequence of medical images from a storage or memory of a computer system (e.g., memory 1710 or storage 1712 of computer 1702 of FIG. 17), or from a remote computer system (e.g., computer 1702 of FIG. 17).

At step 404 of FIG. 4, one or more patches are extracted from each image of the sequence of medical images. The one or more patches may be of any suitable size, such as, e.g., 16×16 pixels.

At step 406 of FIG. 4, spatio-temporal features are extracted from the one or more extracted patches using a machine learning based encoder network. The machine learning based encoder network is trained according to method 100 of FIG. 1 (i.e., trained at step 108 and fine-tuned at step 110) or workflow 200 of FIG. 2. The encoder network receives as input the one or more patches encoded (e.g., combined or concatenated) with positional encodings interpolated from positional encodings determined during the training of the encoder network and generates as output spatio-temporal features. The spatio-temporal features represent spatio-temporal correspondences over space (e.g., location) and time between the patches.

At step 408 of FIG. 4, one or more medical imaging analysis tasks are performed based on the extracted spatio-temporal features. The one or more medical imaging analysis tasks are performed using a machine learning based decoder network and one or more decoder heads. The decoder network receives the spatio-temporal features combined with one or more input query tokens as input and generates one or more output query tokens as output. The one or more output query tokens are combined with the spatio-temporal features and input to the one or more decoder heads, which respectively outputs results of the one or more medical imaging analysis tasks.

At step 410 of FIG. 4, results of the one or more medical imaging analysis tasks are output. For example, the results of the one or more medical imaging analysis tasks can be output by displaying the results on a display device of a computer system (e.g., I/O 1708 of computer 1702 of FIG. 17), storing the results on a memory or storage of a computer system (e.g., memory 1710 or storage 1712 of computer 1702 of FIG. 17) or by transmitting the results to a remote computer system (e.g., computer 1702 of FIG. 17).

Embodiments described herein were experimentally validated. An unlabeled dataset $\mathcal{D}_u$ of coronary x-ray sequences is utilized to pretrain the model. Unlabeled dataset $\mathcal{D}_u$ comprises 241,362 sequences collected from 21,589 patients comprising 16,342,992 frames or images in total. Unlabeled dataset $\mathcal{D}_u$ includes both fluoroscopy ("fluoro") and angiography ("angio") sequences. Ten frames were randomly sampled at a time, with varying temporal gaps between them ranging from 1 to 4 frames. The model is pretrained for 200 epochs with a learning rate of 1e-4.

Figure 5:
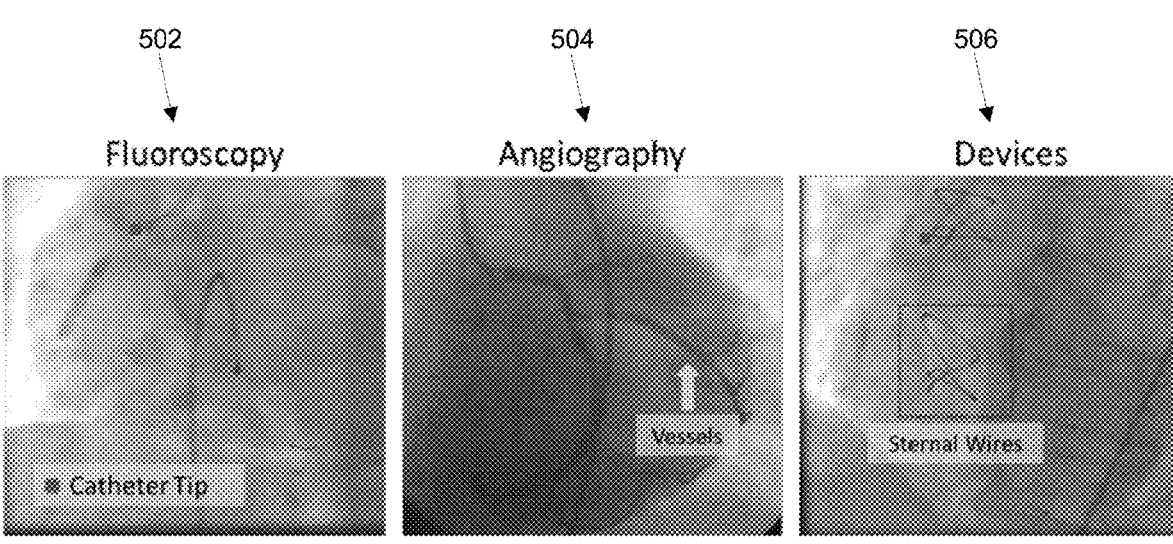
FIG. 5 shows an exemplary fluoroscopy image, angiography image, and devices image depicting a tip of a catheter.

For the downstream task of tracking a tip of a catheter, labeled dataset DI was utilized, where $\mathcal{D}_f \cap \mathcal{D}_u = \emptyset$. The annotations on the frames represent the coordinates of the tip of the catheter, which are converted to Gaussian heatmaps with standard deviation of ~5 mm (millimeters). Mask annotations of the catheter body are also available for a subset of the annotated frames. The training and validation set comprised 2,314 sequences totaling 198,993 frames, out of which 55,957 had annotations. The test set comprised 219 sequences, where all 17,988 frames were annotated. For evaluation, the test set was split into three categories: 94 fluoro sequences (8,494 frames, 82 patients), 101 angio sequences (6,904 frames, 81 patients), and 24 devices sequences (2,593 frames, 10 patients). The category "devices" covers all sequences where sternal wires were present, which cause occlusion, thus further increasing the difficulty of catheter tip tracking. FIG. 5 shows an exemplary fluoroscopy image 502, angiography image 504, and devices image 506 depicting a tip of a catheter. The images were preprocessed using a 160×160 crop for the search image and 64×64 crops for template images. The model was trained for 100 epochs, with a learning rate of 2e-4 using the AdamW optimizer and the Cosine Annealing scheduler with warm resets.

FIG. 6 shows a table 600 comparing the FIMAE (frame interpolation masked autoencoder) approach, implementing embodiments described herein, with conventional approaches. Table 600 compares the FIMAE approach with the following conventional models: SiameseRPN, STARK, MixFormer, Cycle YNet, ConTrack-base, ConTrack-mtmt, and ConTrack-optim. ConTrack-base refers to its base version which has no additional modules, ConTrack-mtmt refers to the multi-task and multi-template version of ConTrack, and ConTrack-optim refers to the final optimal version of ConTrack which has all modules including flow refinement.

As shown in table 600, overall the FIMAE approach demonstrated the best performance on the test dataset, excelling in both precision and robustness. The FIMAE approach significantly reduced the overall maximum error, e.g., by 66.31% against the comparable version of ConTrack (ConTrack-mtmt) and by 23.20% against ConTrack-optim, a highly optimized solution leveraging multi-stage feature fusion, multi-task learning, and flow regularization. In comparison to the other conventional approaches, the FIMAE approach resulted in fewer failures, as depicted by the error distributions in FIG. 7.

FIG. 7 shows graphs of percentile plots tracking error in mm (millimeters). Graph 702 shows a percentile plot comparing tracking error in mm for the 0th to 100th percentile and graph 704 shows a percentile plot comparing tracking error in mm for the 90th to 100th percentile. Graphs 702 and 704 show the error for Cycle YNet 706, ConTrack 708, FIMAE 710, 95th percentile Cycle YNet 712, 95th percentile ConTrack 714, and 95th percentile FIMAE 716. At least 95% of all test cases had an error below the average diameter of the vessels (≈4 mm). Notably, the FIMAE approach stands out from other tracking models by eliminating the need for a two-stage process involving the extraction of spatial features and subsequent matching using feature fusion. Instead, the spatio-temporal encoder in accordance with embodiments described herein jointly performs both.

The other conventional approaches often require two or more forward passes for the two-stage processing to incorporate varying template-search size, which increases computational complexity. This is further amplified by the inclusion of additional modules, such as multi-task decoders and the flow-refinement network in ConTrack-optim. In contrast, the FIMAE model accomplishes the task with a single forward pass for both the multiple templates and the search frame. The only additional modules in the FIMAE model are the two CNN heads for multi-task decoding. This enables the FIMAE model to achieve a significantly higher real-time inference speed of 42 frames per second on a single Tesla V100 GPU (graphics processing unit) without comprising accuracy. Despite Cycle YNet also relying on multiple forward passes for feature extraction, its simplicity and computationally friendly CNN architecture allows it to reach higher speeds, albeit at the expense of accuracy and robustness.

FIG. 8 shows a table 800 comparing the effect of pre-training strategies on the performance of catheter tip tracking. Table 800 compares the performance of the FIMAE approach with the following conventional pretraining methods for sequential image processing: VideoMAE-Kinetics, VideoMAE, and SiamMAE approaches. Pretraining is performed either on an internal dataset (denoted as $\mathcal{D}_u$) or on natural images (for the VideoMAE-Kinetics approach). As shown in Table 2, pretraining on domain-specific data, as opposed to natural images (as used in the VideoMAE-Kinetics approach), offers significant advantages. However, even when including the models trained on $\mathcal{D}_u$ (VideoMAE and SiamMAE) into the comparison, the FIMAE model surpassed all other models by more than 30% across all reported metrics. VideoMAE lacks fine temporal correspondence between frames, leading to non-efficient features matching between template and search frames. SiamMAE relies on only two frames at a time, which is insufficient to fully capture the underlying motion.

Figure 9:
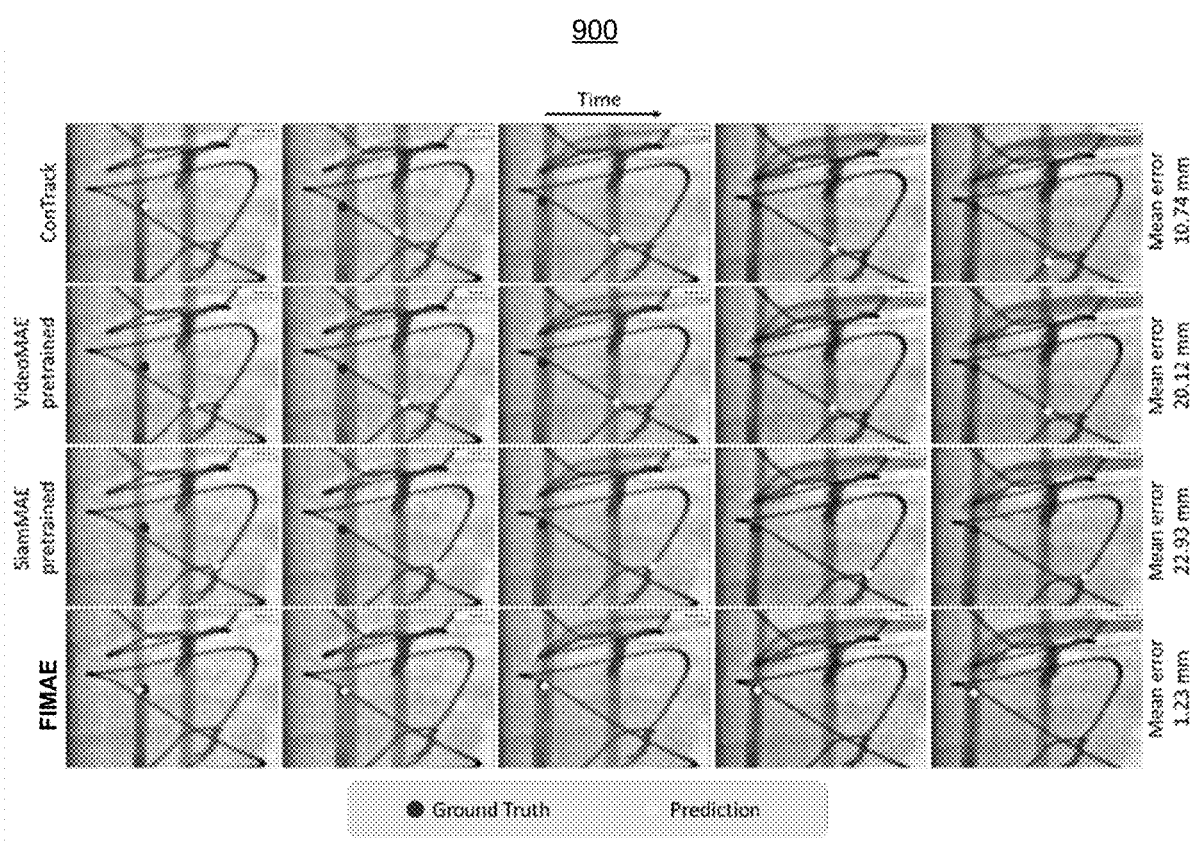
FIG. 9 shows qualitative results comparing a ground truth location of the catheter tip with a predicted location.

FIG. 9 shows qualitative results 900 comparing a ground truth location of the catheter tip with a predicted location. In results 900, the predicted location is predicted according to the FIMAE approach as well as conventional tracking approaches of ConTrack, VideoMAE, and SiamMAE. The predicted locations were predicted on a challenging angiography sequence with contrast-based device obstruction and other visible sternal wires. As shown in results 900, the FIMAE model is able to handle this challenging case by not losing track of the tip of the catheter where other conventional models fail to differentiate the catheter from the sternal wires.

One strength of the FIMAE approach comes from the pretrained spatio-temporal features that facilitate effective feature matching between the template frames and the search frame. Another advantage is its prior understanding of the inherent cardiac/respiratory motion. This knowledge significantly reduces or even eliminates the impact of additional modules such as flow refinement. The FIMAE approach thereby achieves high robustness in tracking, with minimal variations across different additional modules such as multi-task.

Figure 10:
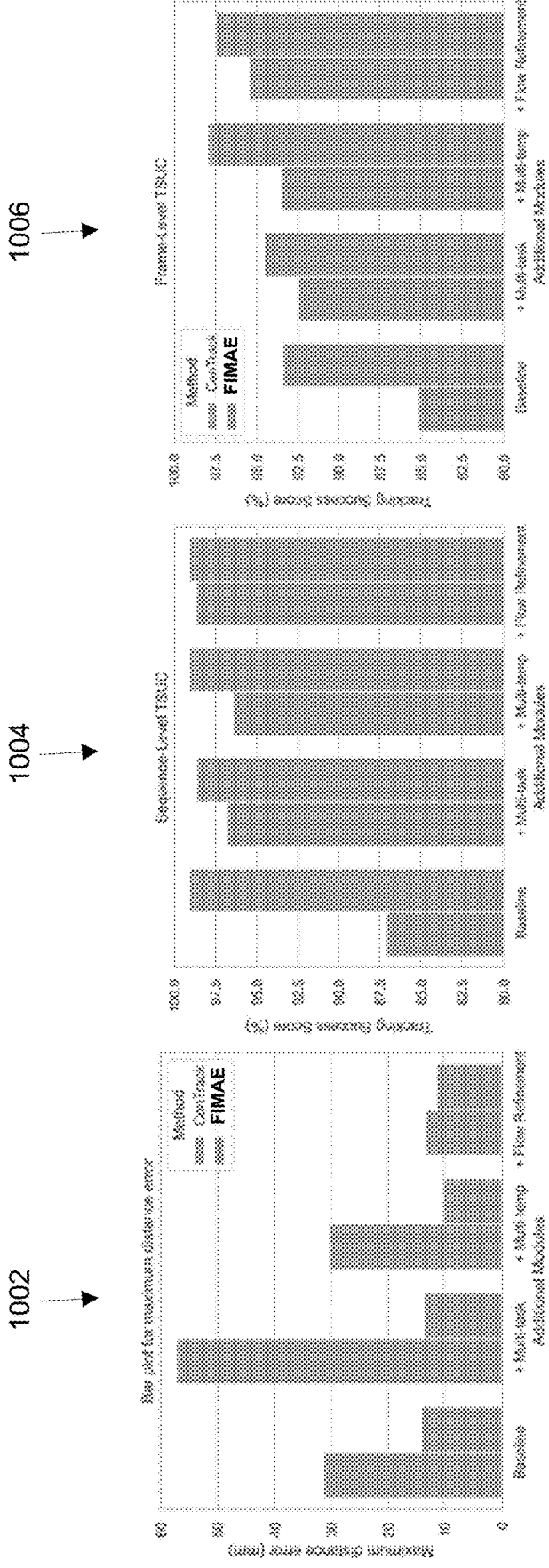
FIG. 10 shows graphs comparing robustness between the FIMAE approach and the ConTrack approach.

FIG. 10 shows graphs comparing robustness between the FIMAE approach and the ConTrack approach. Graph 1002 is a bar plot for maximum distance error (in mm), graph 1004 is a sequence-level TSUC (tracking success score), and graph 1006 is a frame-level TSUC. Graphs 1002, 1004, and 1006 compare the different module configurations of baseline (no additional modules), multi-task module, multi-task and multi-template, and multi-task, multi-template, and flow refinement. The left bar graph in each configuration represents ConTrack results and the right bar graph in each configuration represents the FIMAE results.

Graph 1002 highlights the relative stability of the maximum error across different versions of the FIMAE model compared to the high volatility observed in ConTrack under different module configurations. In addition, ConTrack reaches its best performance only when utilizing all modules, in particular including flow-refinement which in turn leads to increased inference time. Contrary to ConTrack, adding the flow refinement module to the FIMAE model reduced its performance marginally in terms of accuracy (1.54 mm) and robustness (max error of 11.38 mm). This may be attributable to the fact that while flow refinement can propagate noise originating from inaccurately predicted catheter masks.

To further assess the robustness of the tracking systems, tracking success score is introduced. The tracking success score is computed as the ratio of the number of instances (frame or sequence) in which the distance error falls below a specific threshold to the total number of instances. To establish a relevant threshold, the threshold is set at twice the average vessel diameter in the test dataset (≈8 mm). Graphs 1004 and 1006 summarize the results for sequence-level and frame-level tracking success scores respectively. The FIMAE approach consistently achieved a 99.08% sequence-level tracking success score across all additional modules, with only a small drop to 98.61% in the multi-task configuration. At the frame level, the optimal versional of FIMAE (multi-task and multi-template) yields a tracking success score of 97.95%, compared to 93.53% for ConTrack under the same configuration. ConTrack achieves its best frame-level tracking success score of 95.44% using the flow-refinement variant.

FIG. 11 shows percentile plots tracking error in mm for angio cases and for device cases. Graphs 1102 and 1104 show the error for ConTrack-MtMt 1106, ConTrack-Base 1108, ConTrack-Optim 1110, FIMAE 1112, 95th percentile ConTrack-Optim 1114, and 95th percentile FIMAE 1116. In the case of angiography, the FIMAE method showed 15% improved accuracy and 45% reduction in maximum error.

Similarly for the devices (occlusion) category, the FIMAE method showed 43% better accuracy and 60% reduction in maximum error. The FIMAE method performance on angio and devices cases is compared qualitatively with ConTrack in FIG. 12.

Figure 12:
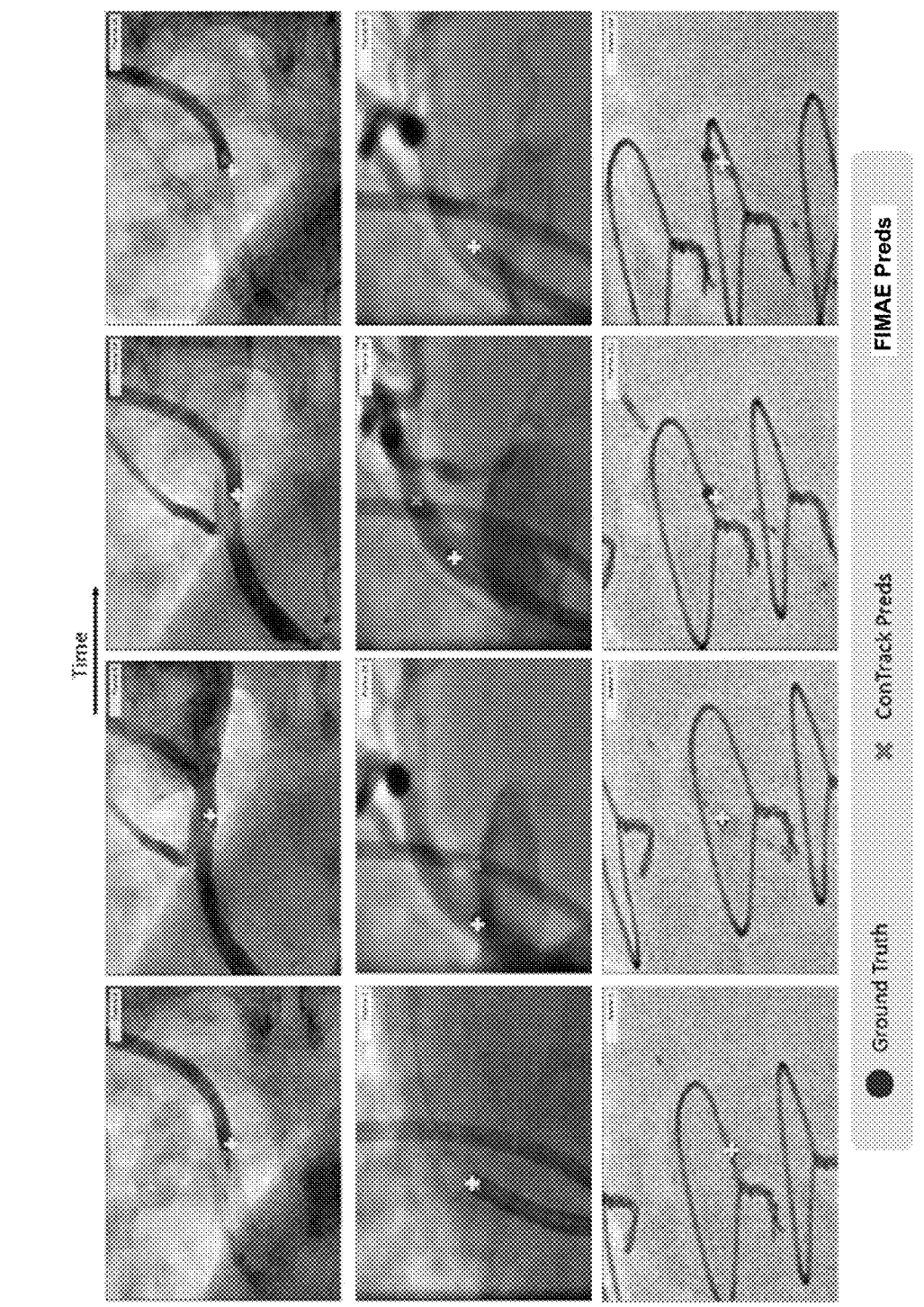
FIG. 12 shows qualitative results comparing ground truth, ConTrack predicted, and FIMAE predicted locations of the catheter tip.

FIG. 12 shows qualitative results 1200 comparing ground truth, ConTrack predicted, and FIMAE predicted locations of the catheter tip in two angio sequences (top two rows) and a device sequence (bottom row). The frames were randomly sampled from the sequence for visualization. Results 1200 shows the effectiveness of the FIMAE approach in the presence of complex occlusions from the vessels and sternal wires. However, ConTrack achieves a better performance in fluoro cases. This may be due to the transformer's architecture, which uses 16×16 patch sizes making it less effective towards faint visibility in low-dose x-rays compared to CNNs.

Ablation studies were also performed to investigate the impact of positional encoding strategies and masking ratios on overall tracking performance.

FIG. 13 shows a table 1300 comparing positional encoding strategies on downstream task performance for the naïve strategy, the learnable strategy, and the frame-aware (FIMAE) strategy. The naïve positional encoding strategy simply applies 1D (one dimensional) sine-cosine positional encoding over all patches, and hence loses the temporal information about the patches resulting in unsatisfactory results. If the learnable positional encoding strategy is used, the temporal positions are still needed to be learnt leading to sub-optimal performance. Interpolating from the central patch positions of the pretrained frames (the frame-aware positional encoding strategy) gives the best results.

FIG. 14 shows a table 1400 of tracking performance of the FIMAE approach trained with different intermediate frame masking ratios (masking ratio of $\Omega_{frame}$). The best results are obtained with an intermediate frame masking ratio of 98%. While the results with 95% frame masking ratio are largely equivalent, there is a notable reduction in performance when the entire frame (100% frame masking ratio) is masked, which may be due to the lack of patches and its relative positions information during pretraining.

Advantageously, embodiments described herein provides for frame interpolation-based masking for capturing fine inter-frame correspondences. The pre-trained spatio-temporal encoder in accordance with embodiments described herein surpasses all conventional pretraining methods for sequential imaging processing. The spatio-temporal features acquired during the pretraining phase significantly influence the extraction and matching of features for the purpose of device tracking. It was demonstrated that an efficient spatio-temporal encoder can replace the Siamese-like architecture, yielding a computationally lightweight model that maintains a high degree of precision and robustness in the tracking task. By adopting the embodiments described herein, a 23.3% reduction in maximum tracking error is achieved, even without the incorporation of supplementary modules such as flow refinement, when compared to conventional multi-modular optimized approaches. The performance enhancement in accompanied by a frame-level tracking success score of 97.95% at 3 times faster inference speed than conventional approaches. The results further show that embodiments described herein achieves superior tracking performance, particularly in the challenging cases where occlusions and distractors are present.

Embodiments described herein are described with respect to the claimed systems as well as with respect to the claimed methods. Features, advantages or alternative embodiments herein can be assigned to the other claimed objects and vice versa. In other words, claims and embodiments for the systems can be improved with features described or claimed in the context of the respective methods. In this case, the functional features of the method are implemented by physical units of the system.

Furthermore, certain embodiments described herein are described with respect to methods and systems utilizing trained machine learning models, as well as with respect to methods and systems for providing trained machine learning models. Features, advantages or alternative embodiments herein can be assigned to the other claimed objects and vice versa. In other words, claims and embodiments for providing trained machine learning models can be improved with features described or claimed in the context of utilizing trained machine learning models, and vice versa. In particular, datasets used in the methods and systems for utilizing trained machine learning models can have the same properties and features as the corresponding datasets used in the methods and systems for providing trained machine learning models, and the trained machine learning models provided by the respective methods and systems can be used in the methods and systems for utilizing the trained machine learning models.

In general, a trained machine learning model mimics cognitive functions that humans associate with other human minds. In particular, by training based on training data the machine learning model is able to adapt to new circumstances and to detect and extrapolate patterns. Another term for "trained machine learning model" is "trained function."

In general, parameters of a machine learning model can be adapted by means of training. In particular, supervised training, semi-supervised training, unsupervised training, reinforcement learning and/or active learning can be used. Furthermore, representation learning (an alternative term is "feature learning") can be used. In particular, the parameters of the machine learning models can be adapted iteratively by several steps of training. In particular, within the training a certain cost function can be minimized. In particular, within the training of a neural network the backpropagation algorithm can be used.

In particular, a machine learning model, such as, e.g., the machine learning based networks utilized at steps 108 and 110 of FIG. 1, encoder 212, decoder 214, encoder 230, decoder 234, heatmap head 240-A, and mask head 240-B of FIG. 2, and the machine learning based networks utilized at step 404 and 406 of FIG. 4, can comprise, for example, a neural network, a support vector machine, a decision tree and/or a Bayesian network, and/or the machine learning model can be based on, for example, k-means clustering, Q-learning, genetic algorithms and/or association rules. In particular, a neural network can be, e.g., a deep neural network, a convolutional neural network or a convolutional deep neural network. Furthermore, a neural network can be, e.g., an adversarial network, a deep adversarial network and/or a generative adversarial network.

Figure 15:
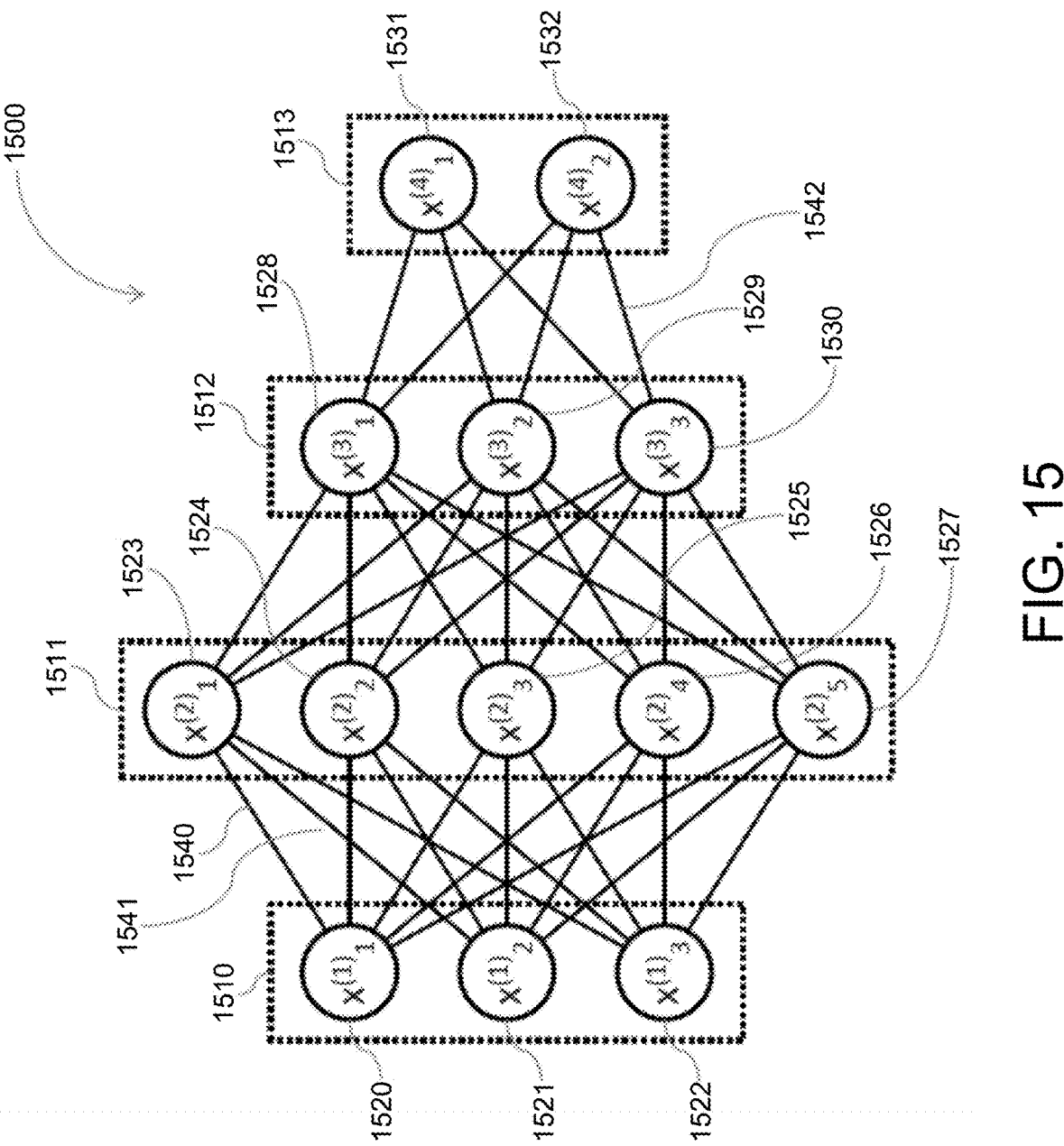
FIG. 15 shows an exemplary artificial neural network that may be used to implement one or more embodiments.

FIG. 15 shows an embodiment of an artificial neural network 1500 that may be used to implement one or more machine learning models described herein. Alternative terms for "artificial neural network" are "neural network", "artificial neural net" or "neural net".

The artificial neural network 1500 comprises nodes 1520, . . . , 1532 and edges 1540, . . . , 1542, wherein each edge 1540, . . . , 1542 is a directed connection from a first node 1520, . . . , 1532 to a second node 1520, . . . , 1532. In general, the first node 1520, . . . , 1532 and the second node 1520, . . . , 1532 are different nodes 1520, . . . , 1532, it is also possible that the first node 1520, . . . , 1532 and the second node 1520, . . . , 1532 are identical. For example, in FIG. 15 the edge 1540 is a directed connection from the node 1520 to the node 1523, and the edge 1542 is a directed connection from the node 1530 to the node 1532. An edge 1540, . . . , 1542 from a first node 1520, . . . , 1532 to a second node 1520, . . . , 1532 is also denoted as "ingoing edge" for the second node 1520, 1532 and as "outgoing edge" for the first node 1520, . . . , 1532.

In this embodiment, the nodes 1520, . . . , 1532 of the artificial neural network 1500 can be arranged in layers 1510, . . . , 1513, wherein the layers can comprise an intrinsic order introduced by the edges 1540, . . . , 1542 between the nodes 1520, . . . , 1532. In particular, edges 1540, . . . , 1542 can exist only between neighboring layers of nodes. In the displayed embodiment, there is an input layer 1510 comprising only nodes 1520, . . . , 1522 without an incoming edge, an output layer 1513 comprising only nodes 1531, 1532 without outgoing edges, and hidden layers 1511, 1512 in-between the input layer 1510 and the output layer 1513. In general, the number of hidden layers 1511, 1512 can be chosen arbitrarily. The number of nodes 1520, . . . , 1522 within the input layer 1510 usually relates to the number of input values of the neural network, and the number of nodes 1531, 1532 within the output layer 1513 usually relates to the number of output values of the neural network.

In particular, a (real) number can be assigned as a value to every node 1520, . . . , 1532 of the neural network 1500. Here, $x^{(n)}_i$ denotes the value of the i-th node 1520, . . . , 1532 of the n-th layer 1510, . . . , 1513. The values of the nodes 1520, . . . , 1522 of the input layer 1510 are equivalent to the input values of the neural network 1500, the values of the nodes 1531, 1532 of the output layer 1513 are equivalent to the output value of the neural network 1500. Furthermore, each edge 1540, . . . , 1542 can comprise a weight being a real number, in particular, the weight is a real number within the interval $[-1, 1]$ or within the interval $[0, 1]$. Here, $w^{(m,n)}_{i,j}$ denotes the weight of the edge between the i-th node 1520, . . . , 1532 of the m-th layer 1510, . . . , 1513 and the j-th node 1520, . . . , 1532 of the n-th layer 1510, . . . , 1513. Furthermore, the abbreviation $w^{(n)}_{i,j}$ is defined for the weight $w^{(n,n+1)}_{i,j}$.

In particular, to calculate the output values of the neural network 1500, the input values are propagated through the neural network. In particular, the values of the nodes 1520, . . . , 1532 of the (n+1)-th layer 1510, . . . , 1513 can be calculated based on the values of the nodes 1520, . . . , 1532 of the n-th layer 1510, . . . , 1513 by $$x^{(n+1)}_j = f\left(\sum_i x^{(n)}_i \cdot w^{(n)}_{i,j}\right).$$

Herein, the function f is a transfer function (another term is "activation function"). Known transfer functions are step functions, sigmoid function (e.g., the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 1510 are given by the input of the neural network 1500, wherein values of the first hid-den layer 1511 can be calculated based on the values of the input layer 1510 of the neural network, wherein values of the second hidden layer 1512 can be calculated based in the values of the first hidden layer 1511, etc.

In order to set the values $w^{(m,n)}_{i,j}$ for the edges, the neural network 1500 has to be trained using training data. In particular, training data comprises training input data and training output data (denoted as $t_i$). For a training step, the neural network 1500 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 1500 (backpropagation algorithm). In particular, the weights are changed according to $$w'^{(n)}_{i,j} = w^{(n)}_{i,j} - \gamma \cdot \delta^{(n)}_j \cdot x^{(n)}_i$$

wherein $\gamma$ is a learning rate, and the numbers $\delta^{(n)}_j$ can be recursively calculated as $$\delta^{(n)}_j = \left(\sum_k \delta^{(n+1)}_k \cdot w^{(n+1)}_{j,k}\right) \cdot f'\left(\sum_i x^{(n)}_i \cdot w^{(n)}_{i,j}\right)$$

based on $\delta^{(n+1)}_j$, if the (n+1)-th layer is not the output layer, and $$\delta^{(n)}_j = \left(x^{(n+1)}_j - t^{(n+1)}_j\right) \cdot f'\left(x^{(n)}_i \cdot w^{(n)}_{i,j}\right)$$

if the (n+1)-th layer is the output layer 1513, wherein f' is the first derivative of the activation function, and $t^{(n+1)}_j$ is the comparison training value for the j-th node of the output layer 1513.

A convolutional neural network is a neural network that uses a convolution operation instead general matrix multiplication in at least one of its layers (so-called "convolutional layer"). In particular, a convolutional layer performs a dot product of one or more convolution kernels with the convolutional layer's input data/image, wherein the entries of the one or more convolution kernel are the parameters or weights that are adapted by training. In particular, one can use the Frobenius inner product and the ReLU activation function. A convolutional neural network can comprise additional layers, e.g., pooling layers, fully connected layers, and normalization layers.

By using convolutional neural networks input images can be processed in a very efficient way, because a convolution operation based on different kernels can extract various image features, so that by adapting the weights of the convolution kernel the relevant image features can be found during training. Furthermore, based on the weight-sharing in the convolutional kernels less parameters need to be trained, which prevents overfitting in the training phase and allows to have faster training or more layers in the network, improving the performance of the network.

Figure 16:
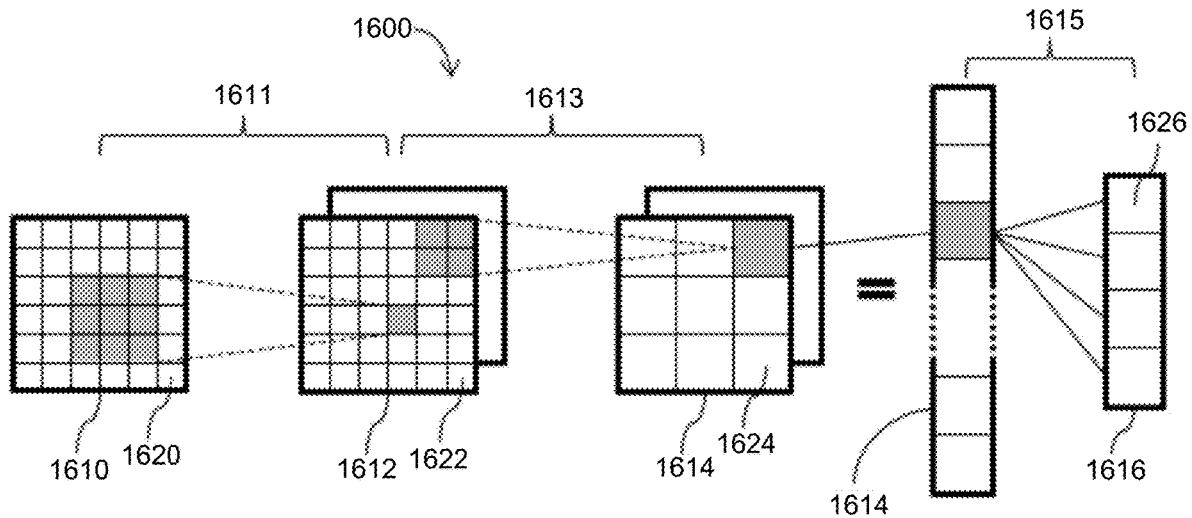
FIG. 16 shows a convolutional neural network that may be used to implement one or more embodiments.

FIG. 16 shows an embodiment of a convolutional neural network 1600 that may be used to implement one or more machine learning models described herein. In the displayed embodiment, the convolutional neural network comprises 1600 an input node layer 1610, a convolutional layer 1611, a pooling layer 1613, a fully connected layer 1614 and an output node layer 1616, as well as hidden node layers 1612, 1614. Alternatively, the convolutional neural network 1600 can comprise several convolutional layers 1611, several pooling layers 1613 and several fully connected layers 1615, as well as other types of layers. The order of the layers can be chosen arbitrarily, usually fully connected layers 1615 are used as the last layers before the output layer 1616.

In particular, within a convolutional neural network 1600 nodes 1620, 1622, 1624 of a node layer 1610, 1612, 1614 can be considered to be arranged as a d-dimensional matrix or as a d-dimensional image. In particular, in the two-dimensional case the value of the node 1620, 1622, 1624 indexed with i and j in the n-th node layer 1610, 1612, 1614 can be denoted as x(n)[i, j]. However, the arrangement of the nodes 1620, 1622, 1624 of one node layer 1610, 1612, 1614 does not have an effect on the calculations executed within the convolutional neural network 1600 as such, since these are given solely by the structure and the weights of the edges.

A convolutional layer 1611 is a connection layer between an anterior node layer 1610 (with node values x(n−1)) and a posterior node layer 1612 (with node values x(n)). In particular, a convolutional layer 1611 is characterized by the structure and the weights of the incoming edges forming a convolution operation based on a certain number of kernels. In particular, the structure and the weights of the edges of the convolutional layer 1611 are chosen such that the values x(n) of the nodes 1622 of the posterior node layer 1612 are calculated as a convolution x(n)=K*x(n−1) based on the values x(n−1) of the nodes 1620 anterior node layer 1610, where the convolution * is defined in the two-dimensional case as $$x_k^{(n)}[i, j] = \left(K * x^{(n-1)}\right)[i, j] = \sum_{i'} \sum_{j'} K\ [i', j'] \cdot x^{(n-1)}[i - i', j - j'].$$

Here the kernel K is a d-dimensional matrix (in this embodiment, a two-dimensional matrix), which is usually small compared to the number of nodes 1620, 1622 (e.g., a 3×3 matrix, or a 5×5 matrix). In particular, this implies that the weights of the edges in the convolution layer 1611 are not independent, but chosen such that they produce said convolution equation. In particular, for a kernel being a 3×3 matrix, there are only 9 independent weights (each entry of the kernel matrix corresponding to one independent weight), irrespectively of the number of nodes 1620, 1622 in the anterior node layer 1610 and the posterior node layer 1612.

In general, convolutional neural networks 1600 use node layers 1610, 1612, 1614 with a plurality of channels, in particular, due to the use of a plurality of kernels in convolutional layers 1611. In those cases, the node layers can be considered as (d+1)-dimensional matrices (the first dimension indexing the channels). The action of a convolutional layer 1611 is then a two-dimensional example defined as $$x^{(n)_b}[i, j] =$$
$$\sum_a K_{a,b} * x^{(n-1)_a}[i, j] = \sum_a \sum_{i'} \sum_{j'} K_{a,b}[i', j'] \cdot x^{(n-1)_a}[i - i', j - j']$$

where $x^{(n-1)_a}$ corresponds to the a-th channel of the anterior node layer 1610, $x^{(n)_b}$ corresponds to the b-th channel of the posterior node layer 1612 and $K_{a,b}$ corresponds to one of the kernels. If a convolutional layer 1611 acts on an anterior node layer 1610 with A channels and outputs a posterior node layer 1612 with B channels, there are A·B independent d-dimensional kernels $K_{a,b}$.

In general, in convolutional neural networks 1600 activation functions are used. In this embodiment re ReLU (acronym for "Rectified Linear Units") is used, with R(z)= max(0, z), so that the action of the convolutional layer 1611 in the two-dimensional example is $$x^{(n)_b}[i, j] = R\left(\sum_a \left(K_{a,b} * x^{(n-1)_a}\right)[i, j]\right) =$$
$$R\left(\sum_a \sum_{i'} \sum_{j'} K_{a,b}[i', j'] \cdot x^{(n-1)_a}[i - i', j - j']\right)$$

It is also possible to use other activation functions, e.g., ELU (acronym for "Exponential Linear Unit"), LeakyReLU, Sigmoid, Tan h or Softmax.

In the displayed embodiment, the input layer 1610 comprises 36 nodes 1620, arranged as a two-dimensional 6×6 matrix. The first hidden node layer 1612 comprises 72 nodes 1622, arranged as two two-dimensional 6×6 matrices, each of the two matrices being the result of a convolution of the values of the input layer with a 3×3 kernel within the convolutional layer 1611. Equivalently, the nodes 1622 of the first hidden node layer 1612 can be interpreted as arranged as a three-dimensional 2×6×6 matrix, wherein the first dimension correspond to the channel dimension.

The advantage of using convolutional layers 1611 is that spatially local correlation of the input data can exploited by enforcing a local connectivity pattern between nodes of adjacent layers, in particular by each node being connected to only a small region of the nodes of the preceding layer.

A pooling layer 1613 is a connection layer between an anterior node layer 1612 (with node values x(n−1)) and a posterior node layer 1614 (with node values x(n)). In particular, a pooling layer 1613 can be characterized by the structure and the weights of the edges and the activation function forming a pooling operation based on a non-linear pooling function f. For example, in the two-dimensional case the values x(n) of the nodes 1624 of the posterior node layer 1614 can be calculated based on the values x(n−1) of the nodes 1622 of the anterior node layer 1612 as $$x^{(n)_b}[i, j] = f\left(x^{(n-1)}[id_1, jd_2], \dots, x^{(n-1)_b}[(i + 1)d_1 - 1, (j + 1)d_2 - 1]\right)$$

In other words, by using a pooling layer 1613 the number of nodes 1622, 1624 can be reduced, by re-placing a number d1·d2 of neighboring nodes 1622 in the anterior node layer 1612 with a single node 1622 in the posterior node layer 1614 being calculated as a function of the values of said number of neighboring nodes. In particular, the pooling function f can be the max-function, the average or the L2-Norm. In particular, for a pooling layer 1613 the weights of the incoming edges are fixed and are not modified by training.

The advantage of using a pooling layer 1613 is that the number of nodes 1622, 1624 and the number of parameters is reduced. This leads to the amount of computation in the network being reduced and to a control of overfitting.

In the displayed embodiment, the pooling layer 1613 is a max-pooling layer, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

In general, the last layers of a convolutional neural network 1600 are fully connected layers 1615. A fully connected layer 1615 is a connection layer between an anterior node layer 1614 and a posterior node layer 1616. A fully connected layer 1613 can be characterized by the fact that a majority, in particular, all edges between nodes 1614 of the anterior node layer 1614 and the nodes 1616 of the posterior node layer are present, and wherein the weight of each of these edges can be adjusted individually.

In this embodiment, the nodes 1624 of the anterior node layer 1614 of the fully connected layer 1615 are displayed both as two-dimensional matrices, and additionally as non-related nodes (indicated as a line of nodes, wherein the number of nodes was reduced for a better presentability). This operation is also denoted as "flattening". In this embodiment, the number of nodes 1626 in the posterior node layer 1616 of the fully connected layer 1615 smaller than the number of nodes 1624 in the anterior node layer 1614. Alternatively, the number of nodes 1626 can be equal or larger.

Furthermore, in this embodiment the Softmax activation function is used within the fully connected layer 1615. By applying the Softmax function, the sum the values of all nodes 1626 of the output layer 1616 is 1, and all values of all nodes 1626 of the output layer 1616 are real numbers between 0 and 1. In particular, if using the convolutional neural network 1600 for categorizing input data, the values of the output layer 1616 can be interpreted as the probability of the input data falling into one of the different categories.

In particular, convolutional neural networks 1600 can be trained based on the backpropagation algorithm. For preventing overfitting, methods of regularization can be used, e.g., dropout of nodes 1620, . . . , 1624, stochastic pooling, use of artificial data, weight decay based on the L1 or the L2 norm, or max norm constraints.

According to an aspect, the machine learning model may comprise one or more residual networks (ResNet). In particular, a ResNet is an artificial neural network comprising at least one jump or skip connection used to jump over at least one layer of the artificial neural network. In particular, a ResNet may be a convolutional neural network comprising one or more skip connections respectively skipping one or more convolutional layers. According to some examples, the ResNets may be represented as m-layer ResNets, where m is the number of layers in the corresponding architecture and, according to some examples, may take values of 34, 50, 101, or 152. According to some examples, such an m-layer ResNet may respectively comprise (m–2)/2 skip connections.

A skip connection may be seen as a bypass which directly feeds the output of one preceding layer over one or more bypassed layers to a layer succeeding the one or more bypassed layers. Instead of having to directly fit a desired mapping, the bypassed layers would then have to fit a residual mapping "balancing" the directly fed output.

Fitting the residual mapping is computationally easier to optimize than the directed mapping. What is more, this alleviates the problem of vanishing/exploding gradients during optimization upon training the machine learning models: if a bypassed layer runs into such problems, its contribution may be skipped by regularization of the directly fed output. Using ResNets thus brings about the advantage that much deeper networks may be trained.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatuses, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatuses, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIG. 1-2 or 4. Certain steps or functions of the methods and workflows described herein, including one or more of the steps or functions of FIG. 1-2 or 4, may be performed by a server or by another processor in a network-based cloud-computing system. Certain steps or functions of the methods and workflows described herein, including one or more of the steps of FIG. 1-2 or 4, may be performed by a client computer in a network-based cloud computing system. The steps or functions of the methods and workflows described herein, including one or more of the steps of FIG. 1-2 or 4, may be performed by a server and/or by a client computer in a network-based cloud computing system, in any combination.

Systems, apparatuses, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIG. 1-2 or 4, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

A high-level block diagram of an example computer 1702 that may be used to implement systems, apparatuses, and methods described herein is depicted in FIG. 17. Computer 1702 includes a processor 1704 operatively coupled to a data storage device 1712 and a memory 1710. Processor 1704 controls the overall operation of computer 1702 by executing computer program instructions that define such operations. The computer program instructions may be stored in data storage device 1712, or other computer readable medium, and loaded into memory 1710 when execution of the computer program instructions is desired. Thus, the method and workflow steps or functions of FIG. 1-2 or 4 can be defined by the computer program instructions stored in memory 1710 and/or data storage device 1712 and controlled by processor 1704 executing the computer program instructions. For example, the computer program instructions can be implemented as computer executable code programmed by one skilled in the art to perform the method and workflow steps or functions of FIG. 1-2 or 4. Accordingly, by executing the computer program instructions, the processor 1704 executes the method and workflow steps or functions of FIG. 1-2 or 4. Computer 1702 may also include one or more network interfaces 1706 for communicating with other devices via a network. Computer 1702 may also include one or more input/output devices 1708 that enable user interaction with computer 1702 (e.g., display, keyboard, mouse, speakers, buttons, etc.).

Processor 1704 may include both general and special purpose microprocessors, and may be the sole processor or one of multiple processors of computer 1702. Processor 1704 may include one or more central processing units (CPUs), for example. Processor 1704, data storage device 1712, and/or memory 1710 may include, be supplemented by, or incorporated in, one or more application-specific integrated circuits (ASICs) and/or one or more field programmable gate arrays (FPGAs).

Data storage device 1712 and memory 1710 each include a tangible non-transitory computer readable storage medium. Data storage device 1712, and memory 1710, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 1708 may include peripherals, such as a printer, scanner, display screen, etc. For example, input/output devices 1708 may include a display device such as a cathode ray tube (CRT) or liquid crystal display (LCD) monitor for displaying information to the user, a keyboard, and a pointing device such as a mouse or a trackball by which the user can provide input to computer 1702.

An image acquisition device 1714 can be connected to the computer 1702 to input image data (e.g., medical images) to the computer 1702. It is possible to implement the image acquisition device 1714 and the computer 1702 as one device. It is also possible that the image acquisition device 1714 and the computer 1702 communicate wirelessly through a network. In a possible embodiment, the computer 1702 can be located remotely with respect to the image acquisition device 1714.

Any or all of the systems, apparatuses, and methods discussed herein may be implemented using one or more computers such as computer 1702.

One skilled in the art will recognize that an implementation of an actual computer or computer system may have other structures and may contain other components as well, and that FIG. 17 is a high level representation of some of the components of such a computer for illustrative purposes.

Independent of the grammatical term usage, individuals with male, female or other gender identities are included within the term.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The following is a list of non-limiting illustrative embodiments disclosed herein:

Illustrative embodiment 1. A computer-implemented method comprising: receiving a sequence of medical images; extracting one or more patches from each image of the sequence of medical images; extracting spatio-temporal features from the one or more extracted patches using a machine learning based encoder network; performing one or more medical imaging analysis tasks based on the extracted spatio-temporal features; and outputting results of the one or more medical imaging analysis tasks, wherein the machine learning based encoder network is trained by: receiving a sequence of training medical images; masking patches of a first set of images of the sequence of training medical images according to a first masking strategy; masking patches of a second set of images of the sequence of training medical images according to a second masking strategy; training the machine learning based encoder network to learn a spatio-temporal relationship between the unmasked patches of the first set of images and the second set of images; and outputting the machine learning based encoder network.

Illustrative embodiment 2. The computer-implemented method of illustrative embodiment 1, wherein the spatio-temporal features represent spatio-temporal correspondences between the one or more patches.

Illustrative embodiment 3. The computer-implemented method of any one of illustrative embodiments 1-2, wherein: masking patches of a first set of images of the sequence of training medical images according to a first masking strategy comprises masking random patches at a same spatial location across the first set of images; and masking patches of a second set of images of the sequence of training medical images according to a second masking strategy comprises masking random patches in each of the second set of images.

Illustrative embodiment 4. The computer-implemented method of any one of illustrative embodiments 1-3, wherein training a machine learning based encoder network to learn a spatio-temporal relationship between the unmasked patches of the first set of images and the second set of images comprises: jointly training the machine learning based encoder network with a machine learning based decoder network for reconstructing the patches of the first set of images and the second set of images.

Illustrative embodiment 5. The computer-implemented method of any one of illustrative embodiments 1-4, wherein the first set of images comprises alternating images of the sequence of training medical images and the second set of images comprises the remaining images of the sequence of training medical images.

Illustrative embodiment 6. The computer-implemented method of any one of illustrative embodiments 1-5, wherein extracting spatio-temporal features from one or more patches extracted from each image of the sequence of medical images using a machine learning based encoder network comprises: encoding the one or more patches with positional encodings determined during the training of the machine learning based encoder network.

Illustrative embodiment 7. The computer-implemented method of any one of illustrative embodiments 1-6, wherein the one or more medical imaging analysis tasks comprises one or more of tracking a tip of a catheter or tracking a catheter in a patient.

Illustrative embodiment 8. An apparatus comprising: means for receiving a sequence of medical images; means for extracting one or more patches from each image of the sequence of medical images; means for extracting spatio-temporal features from the one or more extracted patches using a machine learning based encoder network; means for performing one or more medical imaging analysis tasks based on the extracted spatio-temporal features; and means for outputting results of the one or more medical imaging analysis tasks, wherein the machine learning based encoder network is trained by: receiving a sequence of training medical images; masking patches of a first set of images of the sequence of training medical images according to a first masking strategy; masking patches of a second set of images of the sequence of training medical images according to a second masking strategy; training the machine learning based encoder network to learn a spatio-temporal relationship between the unmasked patches of the first set of images and the second set of images; and outputting the machine learning based encoder network.

Illustrative embodiment 9. The apparatus of illustrative embodiment 8, wherein the spatio-temporal features represent spatio-temporal correspondences between the one or more patches.

Illustrative embodiment 10. The apparatus of any one of illustrative embodiments 8-9, wherein: the means for masking patches of a first set of images of the sequence of training medical images according to a first masking strategy comprises means for masking random patches at a same spatial location across the first set of images; and the means for masking patches of a second set of images of the sequence of training medical images according to a second masking strategy comprises means for masking random patches in each of the second set of images.

Illustrative embodiment 11. The apparatus of any one of illustrative embodiments 8-10, wherein the means for training a machine learning based encoder network to learn a spatio-temporal relationship between the unmasked patches of the first set of images and the second set of images comprises: means for jointly training the machine learning based encoder network with a machine learning based decoder network for reconstructing the patches of the first set of images and the second set of images.

Illustrative embodiment 12. The apparatus of any one of illustrative embodiments 8-11, wherein the first set of images comprises alternating images of the sequence of training medical images and the second set of images comprises the remaining images of the sequence of training medical images.

Illustrative embodiment 13. A non-transitory computer-readable storage medium comprising instructions which, when executed by a computer, cause the computer to carry out operations comprising: receiving a sequence of medical images; extracting one or more patches from each image of the sequence of medical images; extracting spatio-temporal features from the one or more extracted patches using a machine learning based encoder network; performing one or more medical imaging analysis tasks based on the extracted spatio-temporal features; and outputting results of the one or more medical imaging analysis tasks, wherein the machine learning based encoder network is trained by: receiving a sequence of training medical images; masking patches of a first set of images of the sequence of training medical images according to a first masking strategy; masking patches of a second set of images of the sequence of training medical images according to a second masking strategy; training the machine learning based encoder network to learn a spatio-temporal relationship between the unmasked patches of the first set of images and the second set of images; and outputting the machine learning based encoder network.

Illustrative embodiment 14. The non-transitory computer-readable storage medium of illustrative embodiment 13, wherein the spatio-temporal features represent spatio-temporal correspondences between the one or more patches.

Illustrative embodiment 15. The non-transitory computer-readable storage medium of any one of illustrative embodiments 13-14, wherein extracting spatio-temporal features from one or more patches extracted from each image of the sequence of medical images using a machine learning based encoder network comprises: encoding the one or more patches with positional encodings determined during the training of the machine learning based encoder network.

Illustrative embodiment 16. The non-transitory computer-readable storage medium of any one of illustrative embodiments 13-15, wherein the one or more medical imaging analysis tasks comprises one or more of tracking a tip of a catheter or tracking a catheter in a patient.

Illustrative embodiment 17. A computer-implemented method comprising: receiving a sequence of training medical images; masking patches of a first set of images of the sequence of training medical images according to a first masking strategy; masking patches of a second set of images of the sequence of training medical images according to a second masking strategy; training a machine learning based encoder network to learn a spatio-temporal relationship between the unmasked patches of the first set of images and the second set of images; and outputting the machine learning based encoder network.

Illustrative embodiment 18. The computer-implemented method of illustrative embodiment 17, wherein: masking patches of a first set of images of the sequence of training medical images according to a first masking strategy comprises masking random patches at a same spatial location across the first set of images; and masking patches of a second set of images of the sequence of training medical images according to a second masking strategy comprises masking random patches in each of the second set of images.

Illustrative embodiment 19. The computer-implemented method of any one of illustrative embodiments 17-18, wherein training a machine learning based encoder network to learn a spatio-temporal relationship between the unmasked patches of the first set of images and the second set of images comprises: jointly training the machine learning based encoder network with a machine learning based decoder network for reconstructing the patches of the first set of images and the second set of images.

Illustrative embodiment 20. The computer-implemented method of any one of illustrative embodiments 17-19, wherein the first set of images comprises alternating images of the sequence of training medical images and the second set of images comprises the remaining images of the sequence of training medical images.

The invention claimed is:

1. A computer-implemented method comprising:
receiving a sequence of medical images;
extracting one or more patches from each image of the sequence of medical images;
extracting spatio-temporal features from the one or more extracted patches using a machine learning based encoder network;
performing one or more medical imaging analysis tasks based on the extracted spatio-temporal features; and
outputting results of the one or more medical imaging analysis tasks,
wherein the machine learning based encoder network is trained by:
receiving a sequence of training medical images;
masking patches of a first set of images of the sequence of training medical images according to a first masking strategy;
masking patches of a second set of images of the sequence of training medical images according to a second masking strategy;
where in the first masking strategy is different from the second masking strategy;
training the machine learning based encoder network to learn a spatio-temporal relationship between the unmasked patches of the first set of images and the second set of images; and
outputting the machine learning based encoder network.

2. The computer-implemented method of claim 1, wherein the spatio-temporal features represent spatio-temporal correspondences between the one or more patches.

3. The computer-implemented method of claim 1, wherein:
masking patches of a first set of images of the sequence of training medical images according to a first masking strategy comprises masking random patches at a same spatial location across the first set of images; and
masking patches of a second set of images of the sequence of training medical images according to a second masking strategy comprises masking random patches in each of the second set of images.

4. The computer-implemented method of claim 1, wherein training a machine learning based encoder network to learn a spatio-temporal relationship between the unmasked patches of the first set of images and the second set of images comprises:
jointly training the machine learning based encoder network with a machine learning based decoder network for reconstructing the patches of the first set of images and the second set of images.

5. The computer-implemented method of claim 1, wherein the first set of images comprises alternating images of the sequence of training medical images and the second set of images comprises the remaining images of the sequence of training medical images.

6. The computer-implemented method of claim 1, wherein extracting spatio-temporal features from one or more patches extracted from each image of the sequence of medical images using a machine learning based encoder network comprises:
encoding the one or more patches with positional encodings determined during the training of the machine learning based encoder network.

7. The computer-implemented method of claim 1, wherein the one or more medical imaging analysis tasks comprises one or more of tracking a tip of a catheter or tracking a catheter in a patient.

8. An apparatus comprising:
means for receiving a sequence of medical images;
means for extracting one or more patches from each image of the sequence of medical images;
means for extracting spatio-temporal features from the one or more extracted patches using a machine learning based encoder network;
means for performing one or more medical imaging analysis tasks based on the extracted spatio-temporal features; and
means for outputting results of the one or more medical imaging analysis tasks,
wherein the machine learning based encoder network is trained by:
receiving a sequence of training medical images;
masking patches of a first set of images of the sequence of training medical images according to a first masking strategy;
masking patches of a second set of images of the sequence of training medical images according to a second masking strategy;
wherein the first masking strategy is different from the second masking strategy;
training the machine learning based encoder network to learn a spatio-temporal relationship between the unmasked patches of the first set of images and the second set of images; and
outputting the machine learning based encoder network.

9. The apparatus of claim 8, wherein the spatio-temporal features represent spatio-temporal correspondences between the one or more patches.

10. The apparatus of claim 8, wherein:
masking patches of a first set of images of the sequence of training medical images according to a first masking strategy comprises masking random patches at a same spatial location across the first set of images; and
masking patches of a second set of images of the sequence of training medical images according to a second masking strategy comprises masking random patches in each of the second set of images.

11. The apparatus of claim 8, wherein training a machine learning based encoder network to learn a spatio-temporal relationship between the unmasked patches of the first set of images and the second set of images comprises:
jointly training the machine learning based encoder network with a machine learning based decoder network for reconstructing the patches of the first set of images and the second set of images.

12. The apparatus of claim 8, wherein the first set of images comprises alternating images of the sequence of training medical images and the second set of images comprises the remaining images of the sequence of training medical images.

13. A non-transitory computer-readable storage medium comprising instructions which, when executed by a computer, cause the computer to carry out operations comprising:

receiving a sequence of medical images;

extracting one or more patches from each image of the sequence of medical images;

extracting spatio-temporal features from the one or more extracted patches using a machine learning based encoder network;

performing one or more medical imaging analysis tasks based on the extracted spatio-temporal features; and outputting results of the one or more medical imaging analysis tasks, wherein the machine learning based encoder network is trained by:

receiving a sequence of training medical images;

masking patches of a first set of images of the sequence of training medical images according to a first masking strategy;

masking patches of a second set of images of the sequence of training medical images according to a second masking strategy;

wherein the first masking strategy is different from the second masking strategy;

training the machine learning based encoder network to learn a spatio-temporal relationship between the unmasked patches of the first set of images and the second set of images; and outputting the machine learning based encoder network.

14. The non-transitory computer-readable storage medium of claim 13, wherein the spatio-temporal features represent spatio-temporal correspondences between the one or more patches.

15. The non-transitory computer-readable storage medium of claim 13, wherein extracting spatio-temporal features from one or more patches extracted from each image of the sequence of medical images using a machine learning based encoder network comprises:

encoding the one or more patches with positional encodings determined during the training of the machine learning based encoder network.

16. The non-transitory computer-readable storage medium of claim 13, wherein the one or more medical imaging analysis tasks comprises one or more of tracking a tip of a catheter or tracking a catheter in a patient.

* * * * *